US010921888B2

(12) United States Patent
Schiff et al.

(10) Patent No.: US 10,921,888 B2
(45) Date of Patent: Feb. 16, 2021

(54) SENSORY EVOKED RESPONSE BASED ATTENTION EVALUATION SYSTEMS AND METHODS

(71) Applicant: Cornell University, Ithaca, NY (US)

(72) Inventors: Nicholas Schiff, New York, NY (US); Chananel Braiman, New York, NY (US); Chagit Reichenbach, Oak Ridge, TN (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/491,104

(22) PCT Filed: Mar. 2, 2018

(86) PCT No.: PCT/US2018/020703
§ 371 (c)(1),
(2) Date: Sep. 4, 2019

(87) PCT Pub. No.: WO2018/164960
PCT Pub. Date: Sep. 13, 2018

(65) Prior Publication Data
US 2020/0012346 A1 Jan. 9, 2020

Related U.S. Application Data

(60) Provisional application No. 62/468,004, filed on Mar. 7, 2017.

(51) Int. Cl.
*G06F 3/01* (2006.01)
*A61B 5/0484* (2006.01)
*A61B 5/16* (2006.01)

(52) U.S. Cl.
CPC .......... *G06F 3/015* (2013.01); *A61B 5/04845* (2013.01); *A61B 5/168* (2013.01)

(58) Field of Classification Search
CPC . G06F 3/015; A61B 5/04842; A61B 5/04845; A61B 5/168; A61B 5/163; A61B 5/0484; A61B 5/7246
See application file for complete search history.

(56) References Cited

U.S. PATENT DOCUMENTS 4,844,086 A 7/1989 Duffy
5,243,517 A * 9/1993 Schmidt ............... A61B 5/0484
600/544

(Continued)

OTHER PUBLICATIONS

International Search Report and Written Opinion received in PCT Application No. PCT/US2018/020703, dated May 16, 2018.

(Continued)

*Primary Examiner* — Liliana Cerullo
(74) *Attorney, Agent, or Firm* — McDermott Will & Emery LLP

(57) ABSTRACT

The system and methods described herein determine a subject's indication of attention to a first and a second sensory stimuli. The system determines a sensory evoked response of the subject by calculating the statistical relationship between the subject's neural response to the stimuli and a signal feature of the first and the second sensory stimuli. A magnitude value of the sensory evoked response is extracted to determine whether the subject attended-to or ignored the sensory stimuli. The system will select the stimuli that elicited the greater indication of attention, and then trigger further processing by a computer. Such processing can include selecting future content for improving safety warnings, educational materials, or advertisements or further processing can include controlling and navigating a brain computer user interface.

12 Claims, 12 Drawing Sheets

(56) References Cited

U.S. PATENT DOCUMENTS

| | | | |
|---|---|---|---|
| 7,471,978 B2 | 12/2008 | John et al. | |
| 2008/0167571 A1 | 7/2008 | Gevins | |
| 2009/0062681 A1 | 3/2009 | Pradeep et al. | |
| 2009/0327068 A1* | 12/2009 | Pradeep | G16H 10/20 705/14.43 |
| 2012/0083668 A1* | 4/2012 | Pradeep | A61B 5/04015 600/300 |
| 2012/0197153 A1 | 8/2012 | Kraus et al. | |
| 2012/0277548 A1 | 11/2012 | Burton | |
| 2014/0022157 A1* | 1/2014 | Lee | G06F 3/013 345/156 |
| 2015/0248615 A1 | 9/2015 | Parra et al. | |
| 2017/0039591 A1* | 2/2017 | Knight | G06Q 30/0269 |
| 2018/0196511 A1* | 7/2018 | Chae | G06F 3/011 |

OTHER PUBLICATIONS

International Preliminary Report on Patentability received in PCT Application No. PCT/US2018/020703, dated Sep. 10, 2019.
Abdeltawwab, M. M. (2014). Auditory N1-P2 Cortical Event Related Potentials in Auditory Neuropathy Spectrum Disorder Patients. Journal of International Advanced Otology, 10(3), 270-274.
Abrams, D. A., Nicol, T., Zecker, S., & Kraus, N. (2009). Abnormal cortical processing of the syllable rate of speech in poor readers. The Journal of Neuroscience, 29(24), 7686-7693.
Adler G, Adler J, Schneck M, Armbruster B. 1990. Influence of stimulation parameters on auditory stimulus processing in schizophrenia and major depression: An auditory evoked potential study. Acta Psychiatr Scand 81: 453-458.
Adler G, Gattaz WF. 1993. Auditory evoked potentials in schizophrenic patients before and during neuroleptic treatment. Relationship to psychopathological state. Eur Arch Psychiatry Clin Neurosci 242: 357-361.
Ellger, T., Bethke, F., Frese, A., Luettmann, R. J., Buchheister, A., Ringelstein, E. B., & Evers, S. (2002). Event-related potentials in different subtypes of multiple sclerosis—a cross-sectional study. Journal of the neurological sciences, 205 (1), 35-40.
Fein, G., Biggins, C. A., & Mackay, S. (1995). Delayed latency of the event-related brain potential P3A component in HIV disease: Progressive effects with increasing cognitive impairment. Archives of neurology, 52(11), 1109-1118.
Ford JM, Mathalon DH, Kalba S, Marsh L, Pfefferbaum A. 2001. N1 and P300 abnormalities in patients with schizophrenia, epilepsy, and epilepsy with schizophrenialike features. Biol Psychiatry 49: 848-860.
Furdea, A., Halder, S., Krusienski, D. J., Bross, D., Nijboer, F., Birbaumer, N., & Kübler, A. (2009). An auditory oddball (P300) spelling system for brain-computer interfaces. Psychophysiology, 46(3), 617-625.
Giabbiconi, C. M., Dancer, C., Zopf, R., Gruber, T., & Müller, M. M. (2004). Selective spatial attention to left or right hand flutter sensation modulates the steady-state somatosensory evoked potential. Cognitive brain research, 20(1), 58-66.
Horton C, D'Zmura M, Srinivasan R. (2011). EEG reveals divergent paths for speech envelopes during selective attention. International Journal of Bioelectromagnetism 13: 217-222.
Horton, C., D'Zmura, M., & Srinivasan, R. (2013). Suppression of competing speech through entrainment of cortical oscillations. Journal of neurophysiology, 109(12), 3082-3093.
Horton, C., Srinivasan, R., & D'Zmura, M. (2014). Envelope responses in single-trial EEG indicate attended speaker in a 'cocktail party'. Journal of neural engineering, 11(4), 046015.
Howe, A. S., Bani-Fatemi, A., & De Luca, V. (2014). The clinical utility of the auditory P300 latency subcomponent event-related potential in preclinical diagnosis of patients with mild cognitive impairment and Alzheimer's disease. Brain and cognition, 86, 64-74.

Karoumi B, Laurent A, Rosenfeld F, Rochet T, Brunon AM, et al. 2000. Alteration of event related potentials in siblings discordant for schizophrenia. Schizophr Res 41:325-334.
Laurent A, Garcia-Larrea L, d'Amato T, Bosson JL, Saoud M, et al. 1999. Auditory event-related potentials and clinical scores in unmedicated schizophrenic patients. Psychiatry Res 86: 229-238.
Leuthardt, E. C., Schalk, G., Wolpaw, J. R., Ojemann, J. G., & Moran, D. W. (2004). A brain-computer interface using electrocorticographic signals in humans. Journal of neural engineering, 1(2), 63.
Mak, J. N., Arbel, Y., Minett, J. W., McCane, L. M., Yuksel, B., Ryan, D., . . . & Erdogmus, D. (2011). Optimizing the P300-based brain—computer interface: current status, limitations and future directions. Journal of neural engineering, 8(2), 025003.
Muller, M. M., Picton, T. W., Valdes-Sosa, P., Riera, J., Teder-Sälejärvi, W. A., & Hillyard, S. A. (1998). Effects of spatial selective attention on the steady-state visual evoked potential in the 20-28 Hz range. Cognitive Brain Research, 6(4), 249-261.
Phillips, J. M., Maxwell, C. R., Ehrlichman, R. S., & Siegel, S. J. (2009). Event-Related Potentials (ERPs) in the Study of Schizophrenia: How Preclinical ERP Studies have Contributed to our Understanding of Schizophrenia. In Handbook of Neurochemistry and Molecular Neurobiology (pp. 525-543). Springer US.
Schalk, G., & Leuthardt, E. C. (2011). Brain-computer interfaces using electrocorticographic signals. Biomedical Engineering, IEEE Reviews in, 4, 140-154.
Schlor KH, Moises HW, Haas S, Rieger H. 1985. Schizophrenia, psychoticism, neuroleptics, and auditory evoked potentials. Pharmacopsychiatry 18: 293-296.
Schnakers, C., Perrin, F., Schabus, M., Majerus, S., Ledoux, D., Damas, P., . . . & Laureys, S. (2008). Voluntary brain processing in disorders of consciousness. Neurology, 71(20), 1614-1620.
Schreuder, M., Blankertz, B., & Tangermann, M. (2010). A new auditory multi-class brain-computer interface paradigm: spatial hearing as an informative cue. PloS one, 5(4), e9813.
Simpson, T. P., Manara, A. R., Kane, N. M., Barton, R. L., Rowlands, C. A., & Butler, S. R. (2002). Effect of propofol anaesthesia on the event-related potential mismatch negativity and the auditory-evoked potential N1. British journal of anaesthesia, 89(3), 382-388.
Aiken, Steven et al., "Human Cortical Responses to the Speech Envelope," Ear & Hearing 2008, vol. 29, No. 2, 139-157.
Davies, Patricia et al., "Validating the Diagnosis of Sensory Processing Disorders Using EEG Technology," The American Journal of Occupational Therapy 2007, vol. 61, No. 2, 176-189.
Hertrich, Ingo et al., "Magnetic brain activity phase-locked to the envelope, the syllable onsets, and the fundamental frequency of a perceived speech signal," Psychophysiology, 49 (2012), 322-334. Wiley Periodicals, Inc.
Kong, Ying-Yee et al., "Differential modulation of auditory responses to attended and unattended speech in different listening conditions," Hear Res. National Institute of Health, Oct. 2014; 0: 73-81.
Langer, Nicolas et al., "Data Descriptor: A resource for assessing information processing in the developing brain using EEG and eye tracking" CUNY Academic Works, Scientific Data, Apr. 11, 2017.
Mazzini, Letizia et al., "Long-Latency Auditory-Evoked Potentials in Severe Traumatic Brain Injury," American Congress of Rehabilitation Medicine and the American Academy of Physical Medicine and Rehabilitation, Jan. 2001, vol. 82, 57-65.
Picton, T.W. et al., "Human Auditory Evoked Potentials. II: Effects of Attention," Electroencephalography and Clinical Neurophysiology, 1974, 36: 191-199.
Reichenbach, Chagit S. et al., "The Auditory-Brainstem Response to Continuous, Non-repetitive Speech Is Modulated by the Speech Envelope and Reflects Speech Processing," Frontiers in Computational Neuroscience, May 2016, vol. 10, Article 47.
Schulte-Tamburen, A.M. et al., "Comparison of five sedation scoring systems by means of auditory evoked potentials," Intensive Care Med (1999) 25: 377-382.
Trojaborg, W. et al., "Visual and somatosensory evoked cortical potentials in multiple sclerosis," Journal of Neurology, Neurosurgery, and Psychiatry, 1979, 42, 323-330.

(56) References Cited

OTHER PUBLICATIONS

Vecchiato, Giovanni et al., "On the Use of EEG or MEG Brain Imaging Tools in Neuromarketing Research," Hindawi Publishing Corporation, Computational Intelligence and Neuroscience, vol. 2011, Article ID 643489, 12 pages.

Benjamin Meltzer et al., "The steady-state response of the cerebral cortex to the beat of music reflects both the comprehension of music and attention," Frontiers in Human Neuroscience, (vol. 9, 6), Aug. 6, 2015.

\* cited by examiner

SENSORY EVOKED RESPONSE BASED ATTENTION EVALUATION SYSTEMS AND METHODS

RELATED APPLICATIONS

The present application is a United States National Phase under 35 U.S.C. § 371 of International Application No. PCT/US2018/020703, filed on Mar. 2, 2018, which claims priority to, and the benefit of, U.S. Provisional Patent Application No. 62/468,004, entitled "A SENSORY EVOKED RESPONSE ATTENTION INDEX" and filed on Mar. 7, 2017, the entire contents of both of which are hereby incorporated by reference for all purposes.

BACKGROUND

It is difficult to obtain objective measurements of the brain response or attention of subjects to various audio-visual stimuli using existing methods. In medical applications, neuroimaging modalities that may measure attention in command following tasks are expensive, immobile, and temporally imprecise. Biometric methods such as eye tracking, galvanic skin responses, and heart rate monitoring cannot monitor cortical attention of subjects to audio-visual stimuli. Moreover, existing EEG based attention determination methods are unable to directly measure the neural response of subjects to specific attributes in audio-visual stimuli. The system and methods disclosed herein use EEG based attention determination methods to measure a subject's attended-to response for triggering further computer processing, such as a selecting content for future communications or controlling and navigating a brain computer user interface.

SUMMARY OF DISCLOSURE

According to one aspect, the disclosure relates to a method for determining the attention of a subject and triggering computer processing based on the subject's indication of attention. The method includes receiving, by a processor, a measurement of a neural response of the subject to one or more first sensory stimuli and one or more second sensory stimuli, as well as receiving, by the processor, information related to the sensory stimuli, including at least one signal feature. The method also includes determining, by the processor, a statistical relationship between the signal feature of the first sensory stimuli, the second sensory stimuli, and the measurement of the neural response of the subject. In some implementations, the statistical relationship is a cross-correlation analysis between at least one signal feature of the sensory stimuli with the received measurement of the subject's neural response. The signal feature may be an amplitude envelope of natural speech. Next, the method determines magnitude values corresponding to peak values of the determined statistical relationships, and based on the statistical relationships, the method determines, by the processor, an indication of the attention of the subject to the first sensory stimuli and the second sensory stimuli. The method compares the attention indication based on the multiple stimuli and selects content which elicited the greater indication of the subject's attention. In some implementations, the comparison determines whether the subject is paying more attention to the first sensory stimuli compared to the second sensory stimuli, or whether the subject is paying more attention to the second sensory stimuli compared to the first sensory stimuli. The method also includes triggering, by a computer, further processing based on the selection of the content.

In some implementations, the sensory stimuli may include at least one of auditory, visual, or somatosensory stimuli. In some implementations, the sensory stimuli may include a natural conversation speech, a continuous, uninterrupted video stream or stream of photographs, or a continuous, uninterrupted somatosensory sensation, or a combination thereof.

In some implementations, the triggering of further computer processing includes a method for selecting content for future communications based on a mean or medium attention level determined by the sensory evoked response of the subject. In some implementations, the first or second sensory stimuli includes content for future communication related to safety warnings, educational materials, or a portion of an advertisement.

In some implementations, the triggering of further computer processing includes controlling a user interphase, wherein the first sensory stimuli corresponds to a first element of the user interface and the second sensory stimuli corresponds to a second element of the user interface. The method includes selecting the first element if the subject's indication of attention to the first sensory stimuli is greater than their indication to the second sensory stimuli. The method also includes selecting the second element if the subject's indication of attention to the second sensory stimuli is greater than their indication of attention to the first sensory stimuli. In some implementations, the first or second element initiates execution of a software application or software command or generates an electric communication.

According to one aspect, the disclosure relates to a system for determining the attention of a subject and triggering computer processing based on the subject's indication of attention. The system may include a plurality of stimuli devices configured to evoke a neural response of the subject. The system may also include one or more processor implementing a processing unit configured to determine an indication of the attention of the subject to one or more first sensory stimuli and one or more second sensory stimuli. In some implementations, the system receives a measurement of a neural response of a subject to the one or more first sensory stimuli and the one or more second sensory stimuli. The system also receives information related to both sensory stimuli, wherein the information includes at least one signal feature from each sensory stimuli. In some implementations, the system also determines a statistical relationship between the signal feature of the one or more first sensory stimuli, the signal feature of the second sensory stimuli, and the measurements of the subject's neural response. In some implementations, the statistical relationship includes a cross-correlation analysis between the signal feature of the sensory stimuli with the received measurement of the sensory evoked response, wherein the signal feature is an amplitude envelope of natural speech. The system also identifies a first magnitude value corresponding to a peak value of the determined statistical relationship between at least one signal feature of the one or more first sensory stimuli and the measurement of the subject's neural response. The system also identifies a second magnitude value corresponding to a peak value of the determined statistical relationship between at least one signal feature of the one or more second sensory stimuli and the measurement of the subject's neural response. Based on the identified magnitude values, the system determines a first indication of the subject's attention to the one or more first sensory stimuli and a second indication of the subject's attention to the one or more second sensory stimuli based on the identified second magnitude. The system compares the determined first indication of the subject's attention to the determined second indication of the subject's attention and selects content that elicited the greater indication of the attention of the subject. In some implementations, the comparison indicates whether the subject is paying more attention to the first sensory stimuli compared to the second sensory stimuli or vice versa. The system also includes a computer that triggers further computer processing based on the selection of the content.

In some implementations, the sensory stimuli may include at least one of auditory, visual, or somatosensory stimuli. In some implementations, the sensory stimuli may include a natural, conversational speech, a continuous, uninterrupted video stream or stream of photographs, or continuous uninterrupted somatosensory sensations, or a combination thereof.

In some implementations, the computer that triggers further computer processing may include a method for selecting content for future communication based on a mean or median attention level determined by the sensory evoked response of the subject to the first and second sensory stimuli. In some implementations, the sensory stimuli of the system include portions of a safety warning, education materials, or portions of an advertisement.

In some implementations, the computer that triggers further computer processing also includes a method for controlling and navigating a user interface, wherein the first sensory stimuli corresponds to a first element of the user interface and the second sensory stimuli corresponds to a second element of the user interface. In some implementations, the system may select the first element if the subject's indication of attention to the first stimuli is greater than the subject's indication of attention to the second sensory stimuli. In some implementations, the system may select the second element if the subject's indication of attention to the second stimuli is greater than the subject's indication of attention to the first sensory stimuli. In some implementations, the first or the second element initiates execution of a software application or software command, or generates an electric communication.

BRIEF DESCRIPTION OF THE DRAWINGS

The foregoing will be apparent from the following more particular description of example implementations of the invention, as illustrated in the accompanying drawings. The drawings are not necessarily to scale, emphasis instead being placed upon illustrating implementations of the present invention.

For purposes of clarity, not every component may be labeled in every figure. The drawings are not intended to be drawn to scale. Like reference numbers and designations in the various figures indicate like elements.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Systems and methods according to the present disclosure relate to the use of the sensory evoked response to naturalistic sensory stimuli as an electroencephalography (EEG), electrocorticography (ECoG) or magnetoencephalography (MEG) based index of attention of a subject to sensory stimuli. In some implementations, the sensory evoked response signal features of attended-to attributes in the naturalistic sensory stimuli are compared to the sensory evoked response of unattended-to attributes. Attention enhances the magnitude of the sensory evoked response signal, suppresses the neural response to the ignored sensory stream, modulates the spatial distribution of the sensory evoked response, and shifts the latency of the sensory evoked response. Accordingly, the sensory evoked response can be compared by comparing the magnitudes of peak values in the corresponding sensory evoked response signals for attended-to and ignored paradigms. In some implementations, the EEG activation may also be compared to the eye tracking response to the naturalistic sensory stimuli. In some implementations, the location and duration of the eye tracking may be compared to the sensory evoked attention response. The sensory evoked response may also reveal the strength and the duration of the neural response of a subject to specific features of the naturalistic sensory stimuli. In some implementations, the sensory evoked response is measured to one or more auditory stimuli, such as naturalistic speech. In some implementations, the sensory evoked response is measured to one or more auditory and visual stimuli.

In some implementations, systems and methods according to the present disclosure provide an EEG- or ECoG-based Brain Computer Interface (BCIs) for touch-free mind-controlled devices. Touch-free mind-controlled devices may be navigated or controlled through a user intentionally attending to various sensory stimuli. A further discussion of brain computer user interfaces is below.

In some implementations, systems and methods according to the present disclosure relate to selecting content for future communications. In some implementations, the selection of content for future communications may relate to content for improving safety warnings, content for improving educational materials, or content for improving marketing materials. A further discussion of the method for selecting content for future communication is below in FIG. 10.

Figure 1:
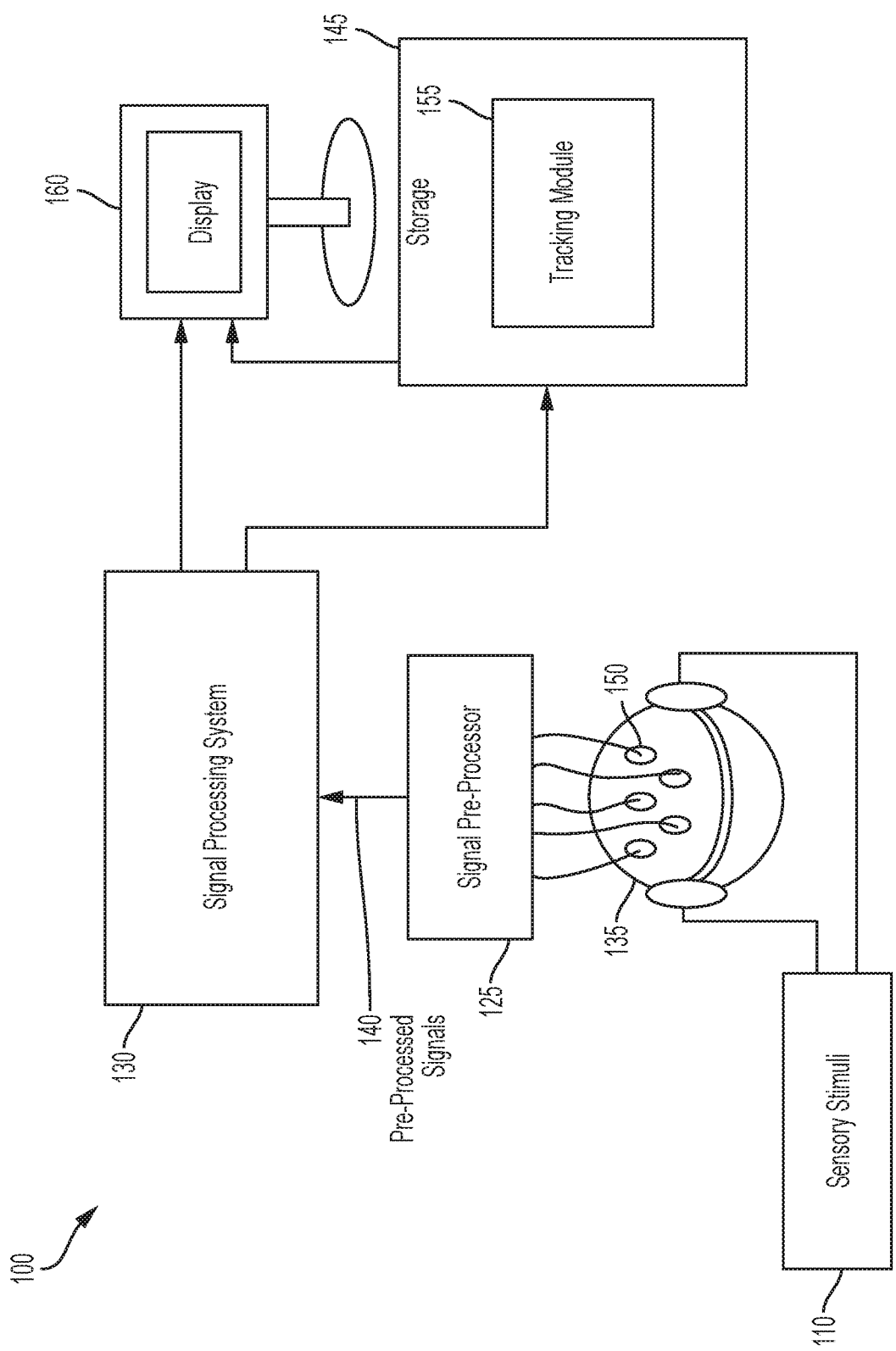
FIG. 1 is a diagram of an environment in which an indication of the attention of the subject to sensory stimuli is provided according to an example implementation.

FIG. 1 is a diagram of an environment 100 in which an indication of attention of a subject 135 to sensory stimuli 110 is provided according to an example implementation. In FIG. 1, the subject 135 is presented with a naturalistic sensory stimuli 110. The naturalistic sensory stimuli 110 may be an audio-visual stimuli composed of natural speech, music, or other sounds and/or visual images or video. In some implementations, the naturalistic stimuli are personally meaningful or encountered in the subject's 135 environmental setting. In some implementations, the auditory naturalistic stimulus 110 presented to the patient subject 135 is composed of natural speech. In some implementations, natural speech refers to natural, continuous oral speech. In some implementations, natural speech refers to speech in a dialogue. In some implementations, natural speech refers to speech demonstrating the grammatical or diction nuances of spoken (as opposed to read aloud) language. In some implementations, the naturalistic sensory stimulus 110 is a visual stimulus. In some implementations, the naturalistic visual stimulus may be a continuous, uninterrupted video stream. In some implementations, the naturalistic stimuli are a combination of auditory, visual, and somatosensory stimuli.

The environment 100 also includes a sensing system 150. The sensing system 150 includes sensors to record the neural data. In some implementations, the sensing system 150 is an EEG or ECoG based system. The sensing system 150 is positioned on the scalp of the patient subject 135 and measures the brain signals (i.e., EEG activity) of the subject 135 in response to the naturalistic audio-visual sensory stimulus 110. The EEG activity of the subject 135 is measured in response to the auditory stimuli, somatosensory, and/or the visual stimuli. The signal acquired by the sensor is amplified, filtered, and digitized via an analog-to-digital converter. In some implementations, the sensing system 150 may have 24 or 7 EEG sensors positioned along the International 10/20 system.

The environment 100 also includes a signal pre-processor 125. The signal pre-processor 125 removes artifacts from the brain signals acquired by the sensing system 150. In some implementations, artifacts may be removed by visual inspection. In other implementations, values that exceed a certain amplitude may be considered artifacts. The signal pre-processor 125 also samples the brain signals acquired by the sensing system 150. The signal pre-processor 125 generates a set of pre-processed brain signals 140. In some implementations, the signal pre-processor 125 may utilize an independent component analysis (ICA) for artifact removal. In some implementations, the signal pre-processor 125 samples the acquired brain signals at a sampling rate that is equal to or above 250 Hz. In some implementations, the signal pre-processor 125 may also include an amplifier, a digitizer and an application programming interface (API).

The environment 100 also includes a signal processing system 130. The pre-processed brain signals 140 and the sensory stimuli 110 are input into the signal processing system 130. The signal processing system 130 processes the pre-processed brain signals 140 in order to compute a sensory evoked response of the subject 135 to the naturalistic audio-visual sensory stimuli 110. The signal processing system 130 computes the sensory evoked response by cross correlating (or calculating another similar statistical comparison of) the pre-processed brain signals 140 and signals associated with the naturalistic audio-visual sensory stimuli 110. Signal features of the resulting sensory evoked response such as latencies of peaks, peak amplitudes, polarities, and spatial distribution may be measured. The magnitude of the peaks of the sensory evoked response signal, the latencies, and modulations of the spatial distribution of the sensory evoked response signal can be employed as the indicators of the attention of the subject 135 to the naturalistic sensory stimuli 110. The spatial distribution of the sensory evoked response signal is the distribution of the strength of the EEG signal across the sensors positioned on various locations on the subject's scalp. The spatial distribution indicates which part of the brain is producing the strongest response to a sensory stimulus. The spatial distribution of the sensory evoked response may differ across subjects. The spatial distribution of the sensory evoked response signal may be modulated by attention.

Figure 10:
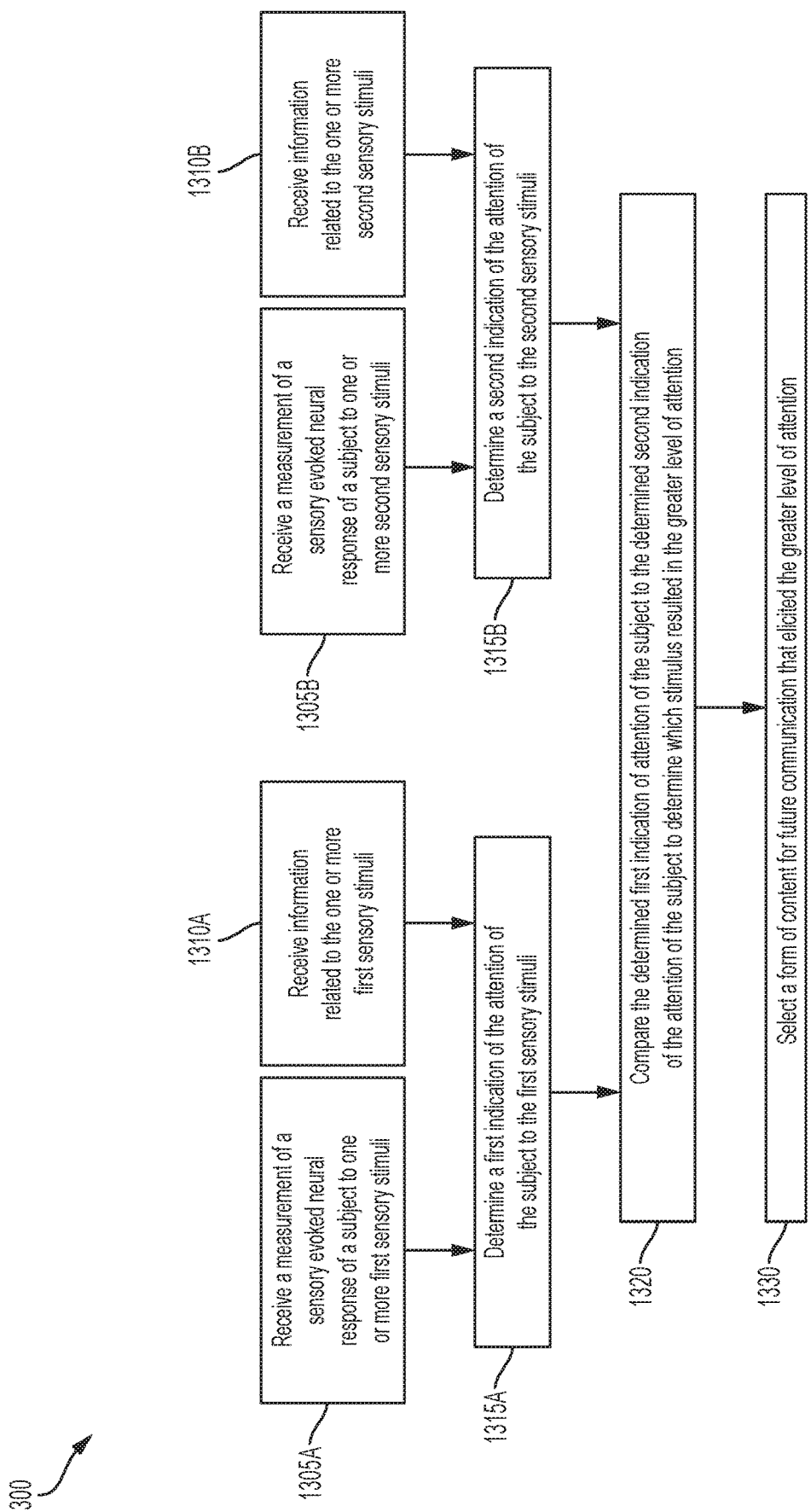
FIG. 10 illustrates a flow diagram of an example method for selecting content for future communication based on the subject's indication of attention.

In some implementations, a baseline indication of attention of the subject can be established by measuring the spatial distribution of the sensory evoked response while directing the subject to focus on different features of the sensory stimuli. In some implementations, a machine learning approach may be utilized to establish a baseline indication of attention of the subject by measuring the spatial distribution of the subject's sensory evoked response to various sensory stimuli. In some implementations, the signal features selected as inputs to the machine learning algorithms may correspond to the channels with the strongest sensory evoked response or the greatest difference in the sensory evoked response between attend and ignore conditions. In some implementations, the machine learning algorithm may identify the most informative channels for classification of attention. In some implementations, the sensory evoked response to different naturalistic stimuli may be used to select a form of content for communication. Further details describing the method of selecting content for communication are shown in FIG. 10 below.

The environment 100 also includes a memory storage unit 145, a tracking module 155, and a display 160. In some implementations, the signal processing system 130 may store its data and results in the memory storage unit 145 for offline analysis. In some implementations, the stored data in the memory storage unit 145 may be tracked over time through the tracking module 155. The tracking module 155 may track multiple measurements of the sensory evoked response based on different naturalistic sensory stimuli or different trials of the same naturalistic sensory stimuli over time. In some implementations, the tracking module 155 may track the sensory evoked response of multiple people to the same naturalistic sensory stimuli 110. In some implementations, the signal processing system 130 may dynamically compute and present the real-time results on the display 160. In some implementations, the results may include the signal features, and the classification of the attention, working memory, comprehension and/or familiarity response of the subject to the sensory stimuli. For tracking purposes, any of the features of the sensory evoked response, including latencies, amplitudes, polarities, and spatial distribution may be stored in the storage 145 over time, and compared by the signal processing system 130 or a system user. The results of the comparison can be displayed on the display 160, for example as a trend line, a graph, or a textual or graphical representation of the comparison results.

The analysis of the subject's attention data may be provided by a computer and outputted by the computer. Details describing the methods of the computer system are described further in FIG. 9 below.

In some implementations, systems and methods according to the present disclosure may supplement traditional approaches to measuring attention such as eye tracking and functional magnetic resonance imagery (fMRI) scans. In some implementations, the systems and methods according to the present disclosure may supplement traditional behavioral assessments such as focus groups, facial coding, surveys, questionnaires, and other measures of advertisement effectiveness testing, such as, but not limited to, recall, recognition, and persuasion tests. In some implementations, attributes of visual stimuli may be modulated with a unique superimposed time series. In some implementations, the cortical response of a subject to the natural speech envelope of speech or multiple streams of speech may be measured.

In some implementations, for auditory stimuli, the neural response to speech may be measured. Attention to different segments of speech or words enhances the sensory, evoked response, suppresses the sensory evoked response of any unattended sensory stream, and may modulate the latency and spatial distribution of the sensory evoked response. In some implementations, the sensory evoked response may be compared to results attained from neuroimaging modalities such as PET scans, fMRI/MRI scans, and CT scans in addition to clinical evaluations, such as a CRS-R behavioral assessment.

Figure 2:
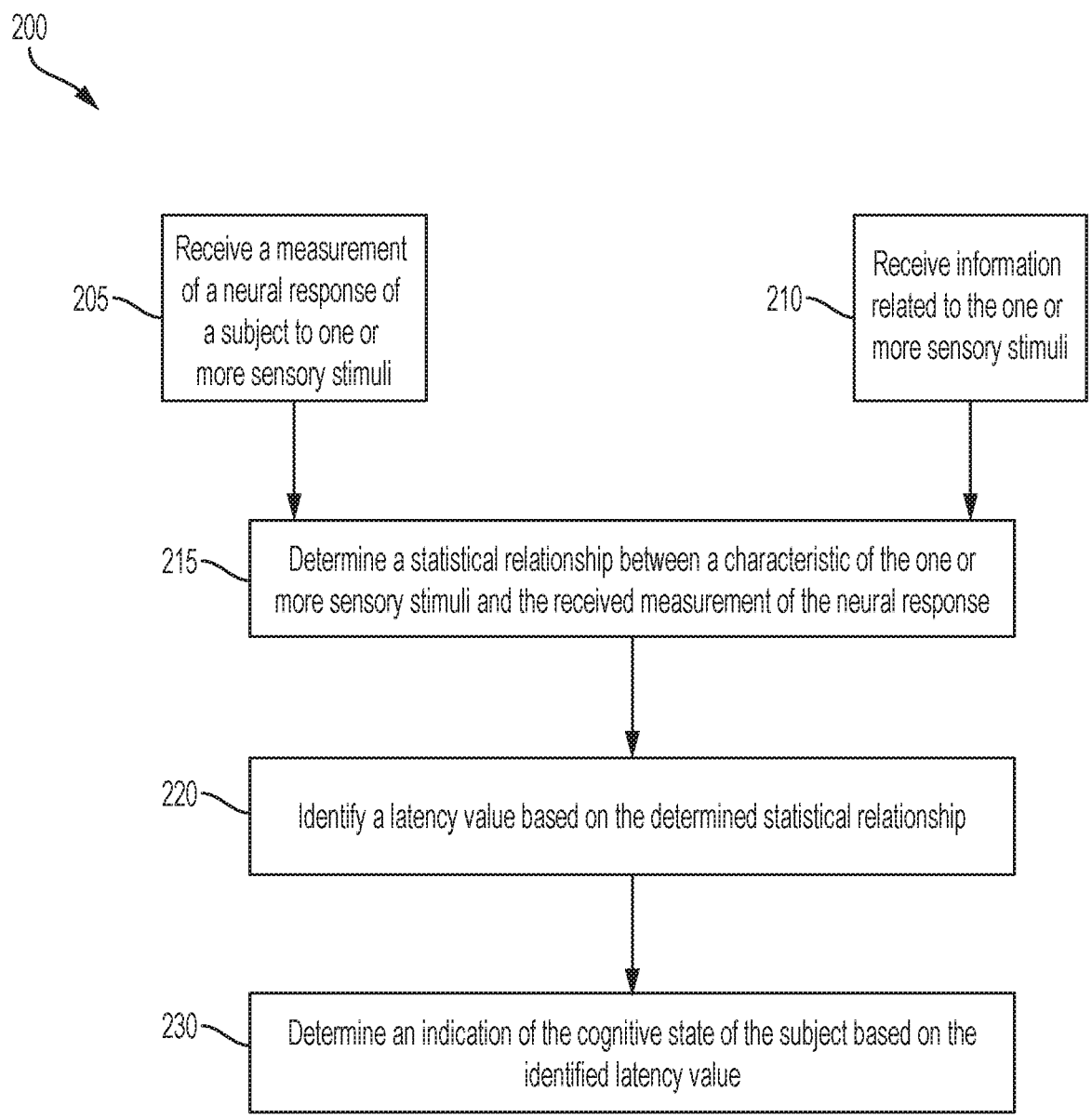
FIG. 2 shows a flow diagram of a method for providing an indication of the attention of the subject to sensory stimuli.

FIG. 2 illustrates a flow diagram of an example method 200 for providing an indication of the attention of a subject to naturalistic sensory stimuli according to an example implementation. The method 200 includes receiving a measurement of a neural response of a subject 135 to sensory stimuli 110 (step 205). The method 200 also includes receiving information related to the one or more sensory stimuli 110 that generated the neural response in step 205 (step 210). The method 200 includes determining a statistical relationship between a characteristic of the one or more sensory stimuli and the received measurement of the neural response (step 215). This signal representing this statistical relationship over various latencies is referred to as the "sensory evoked response" signal. The method 200 includes identifying a magnitude value corresponding to a peak value based on the determined statistical relationship (step 220). The method 200 further includes determining an indication of the attention of the subject to the sensory stimuli based on the identified magnitude value (step 230).

Referring to FIGS. 1 and 2, first the method 200 includes receiving a measurement of a neural response of a subject 135 to one or more sensory stimuli 110 (step 205). In some implementations, the sensory stimuli can be audio-visual stimuli. The neural response of a subject can be measured by the sensing system 150. In some implementations, the received measurement of the neural response may be the preprocessed brain signals 140. The method 200 also includes receiving information related to the one or more sensory stimuli 110 that generated the neural response (step 210). As mentioned above, the sensory stimuli 110 may be an audio-visual stimulus composed of natural speech, music, or other sounds and/or continuous visual images or video, or period or quasi periodic audio, visual, or somatosensory stimuli.

The method 200 includes determining a statistical relationship between a characteristic of the one or more sensory stimuli 110 and the received measurement of the neural response (step 215), such as the pre-processed brain signals 140. In some implementations, the sensory stimuli 110 may be periodic, quasi-periodic, or aperiodic. Naturalistic stimuli are examples of aperiodic signals. In some implementations, the sensory stimuli may be composed of predominantly lower frequency components or predominantly higher frequency components with slower modulation frequency components. For sensory stimuli with predominantly lower frequency components, e.g., below 50 Hz, the statistical relationship is determined by cross-correlating the time series of the measured EEG neural response of the subject, such as the pre-processed brain signals 140, with the raw time series corresponding to the sensory stimuli 110. For sensory stimuli including higher frequency components (such as speech), the cross-correlation or some other statistical comparison is generated based on the envelope of the stimulus signal. The magnitude of the Hilbert transform of the stimulus time series determines the sensory envelope. As indicated above, a sensory evoked response of the subject is a signal representation of a statistical comparison between the EEG neural response signal and either the raw stimulus signal or the signal envelope.

In some implementations, the sensory stimuli signal may be band-pass filtered. In some implementations, the EEG signal is band-pass filtered in the range of 2-30 Hz. In some implementations, the EEG signal is band-pass filtered in the range of 1-90 Hz. The sensory stimuli and the EEG signals are resampled to have matching sampling rates. The EEG signal and the sensory stimuli from each trial are segmented into epochs and their cross-correlation, r, is computed by the following formula:

$$r = \frac{\sum_i [(x(i) - mx) * (y(i-d) - my)]}{\sqrt{\sum_i (x(i) - mx)^2} \sqrt{\sum_i (y(i-d) - my)^2}}$$

In the formula, y represents the time series of the sensory stimulus input, x represents the EEG signal time series for each EEG channel, my represents the mean of the sensory stimuli time series, and mx represents the mean of the EEG signal time series. Individual averages are determined by computing the mean of the cross-correlations between the EEG signal time series and the sensory stimulus input time series across all segments.

The statistical significance of the cross-correlations may be ascertained by the following approach. The cross-correlation values for each of the cross-correlation functions for each epoch are randomly redistributed and the mean of the chance cross-correlations calculated. The values in the average random cross-correlation function are grouped across time and channels forming an approximately normal distribution. In some implementations, peak values of the cross-correlation function can be compared with control randomized cross-correlations computed by randomly redistributing the values of each cross-correlation segment between the natural speech envelope and the EEG neural response across the time points and averaging across the segments. A 95% confidence range of control cross-correlation values can be determined through the mean and standard deviation of the above resultant distribution. Peak values that exceed the natural speech envelope and neural response EEG cross-correlation function that exceed the 95% confidence interval are deemed statistically significant at p<0.05 following False Discovery Rate multiple comparisons. In some implementations, the standard deviation or standard error of the mean of the sensory evoked response can be computed across multiple segments of cross-correlation functions between the natural speech envelope or other naturalist stimuli and the EEG neural response.

In some implementations, other forms of statistical relationships known by persons having ordinary skill in the art may also be used in step 215. For example, in some implementations, the statistical relationship may be a regression analysis.

Referring back to FIGS. 1 and 2, the method 200 includes identifying a magnitude value corresponding to a peak value based on the determined statistical relationship from step 215 (step 220). As described above, in some implementations, the determined statistical relationship is calculated as the cross-correlation between the stimulus signal 110 and the resulting neural response. In some implementations, the sensory evoked response of the subject resulting from the sensory stimuli 110 may be composed of a series of recurring peaks. The peak amplitude of the statistical relationship between the naturalistic stimulus signal and the neural response is used as the magnitude value referred to above. In some implementations, the method 200 includes identifying signal features other than magnitude based on the determined statistical relationship. In some implementations, the additional signal features can include the latency and spatial distribution of the sensory evoked response. For sensory stimuli that are periodic, the cross-correlation of the periodic signal with the EEG response results in a sensory evoked response with recurring peaks, whereby the latency of any of the peaks may correspond to the delay of the brain response and the amplitude is the amplitude of the response. The delay between the peaks corresponds to the periodicity of the stimulus. For sensory stimuli that are aperiodic the resulting sensory evoked response may have multiple peaks in the resultant response, wherein each peak's latency and amplitude correspond to a separate delay of the brain's processing of the signal. For sensory stimuli containing auditory stimuli, such as natural speech, the resulting sensory evoked response based on the cross-correlation analysis of the EEG signal and the speech envelope reveals peaks at latencies of approximately 90 ms, 200 ms, 320 ms, and 450 ms. A similar sensory evoked response may be obtained in the visual and somatosensory modalities. The signal features of the sensory evoked response that may be employed as an index of attention include the latencies and the delay between peaks, the amplitudes or magnitudes of the peaks, the polarities, and the spatial distribution of the sensory evoked response.

In some implementations, a preferred region of interest of the brain is selected for evaluation by monitoring multiple regions of interest, each composed of a sensory channel and its immediate neighboring electrodes. The neural response and sensory evoked response may be obtained and calculated for each region of interest, and the region showing the highest magnitude peaks or having the greatest definition may be used for further analysis.

Referring back to FIGS. 1 and 2, the method 200 further includes determining an indication of the subject's 135 attention to the one or more sensory stimuli 110 based on the identified magnitude value in step 220 (step 320). As mentioned above, the signal features of the computed sensory evoked response may be measured and may individually or in combination classify attention. In some implementations, the signal features may include the latencies of peaks, the peak amplitude or magnitudes, polarities, or the spatial distribution. The attention of the subject 135 to sensory stimuli may enhance the magnitude of the sensory evoked response signal, suppress the neural response to the unattended sensory stimuli, modulate the spatial distribution of the sensory evoked response signal, or shift the latency of the sensory evoked response. Accordingly, the magnitude of the peaks of the sensory evoked response signal, and/or the spatial distribution and/or the latencies of the sensory evoked response signal, can be employed as indicators of the attention of the subject to the sensory stimuli. In some implementations, the method 200 further includes determining an indication of the attention of the subject to the sensory stimuli based on the identified magnitude value of the sensory evoked response, as well as the additional signal features mentioned above. In some implementations, the method 300 may include selecting a form of content which elicited the greater indication of the attention of the subject. The method of selecting the form of content that elicited the greater indication of the attention of the subject is explained in further detail in FIGS. 3 and 10 below.

Figure 3:
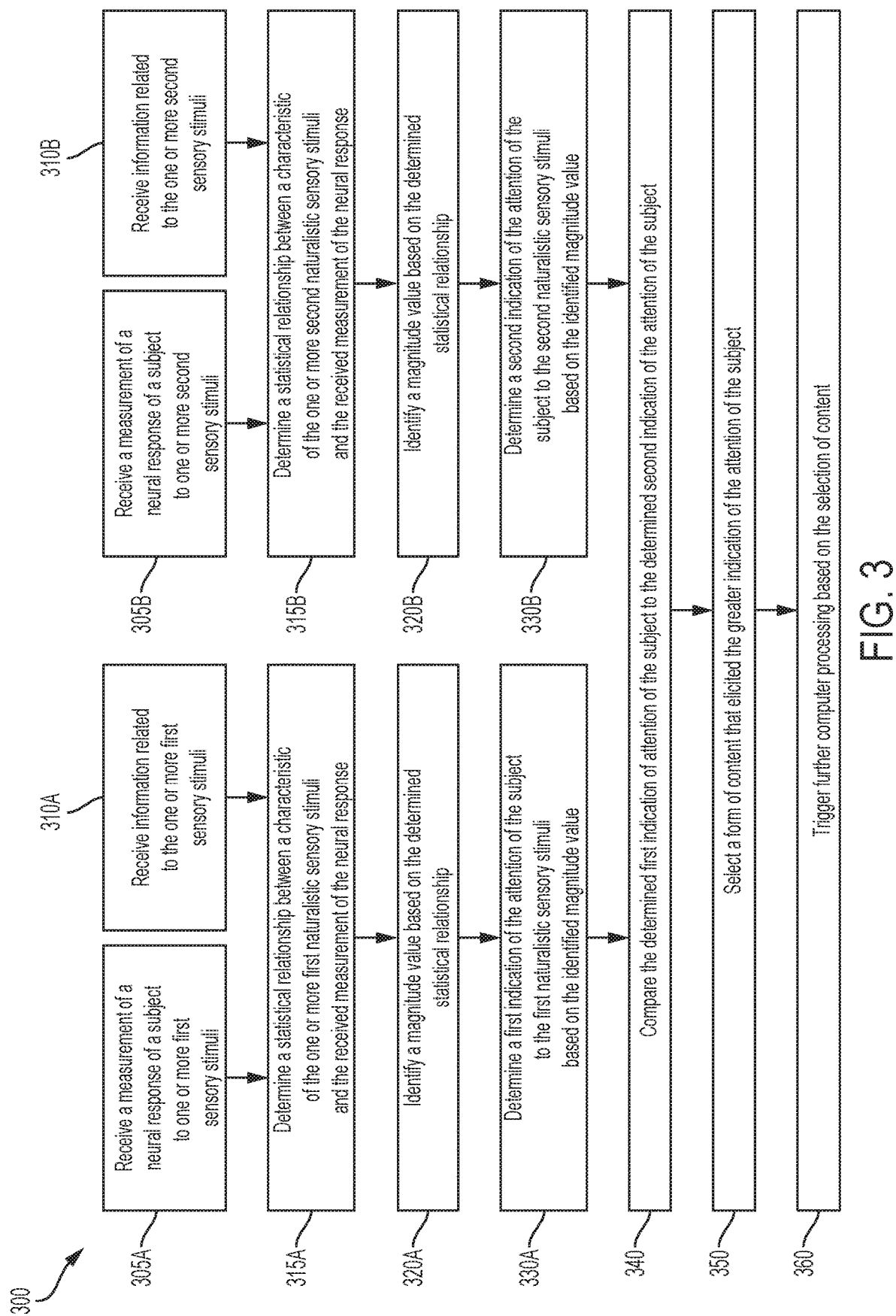
FIG. 3 shows a flow diagram of a method for selecting the more attended to content of a subject when presented with first and second sensory stimuli according to an example implementation.

FIG. 3 shows a flow diagram of an example method 300 for evaluating of the attention of a subject between two sensory stimuli according to the example implementations described above. The method 300 includes receiving a measurement of a first neural response of a subject to a first sensory stimuli (step 305A) and a measurement of a second neural response of a subject to a second sensory stimuli (step 305B). The method 300 also includes receiving information related to the first sensory stimuli (step 310A) and the second sensory stimuli (step 310B) that generated the first and second neural responses. The method 300 includes determining a first statistical relationship between a characteristic of the one or more first sensory stimuli and the received measurement of the first neural response (step 315A). The method 300 includes determining a second statistical relationship between a characteristic of the one or more second sensory stimuli and the received measurement of the second neural response (step 315B). The method 300 includes identifying a first magnitude value corresponding to a peak value based on the first determined statistical relationship (step 320A) and identifying a second magnitude value corresponding to a peak value based on the second determined statistical relationship (step 320B). The method 300 further includes determining a first indication of the attention of the subject to the first sensory stimuli based on the first identified magnitude value (step 330A) and determining a second indication of the attention of the subject to the second naturalistic sensory stimuli based on the second identified magnitude value (step 330B). The method 300 includes comparing the determined first indication of attention of the subject to the determined second indication of the attention of the subject (step 340). The method 300 further includes selecting a form of content which elicited the greater indication of the attention of the subject (step 350) and, triggering further computer processing based on the selection of content (step 360). In some implementations, selecting the form of content which elicited the greater indication of the attention of the subject can indicate which stimulus the subject is paying more attention to. In some implementations, the triggering of further computer processing includes building content for future communications, such as content for improving safety warnings, content for improving educational materials, or content for improving marketing materials. Systems and methods for selecting a form of content for future communications are discussed further below in FIG. 10.

In some implementations, triggering further computer processing may be used for controlling and navigating a brain computer user interface. In some implementations, the first sensory stimuli can correspond to a first element of a user interface and the second sensory stimuli can correspond to a second element of the user interface. In some implementations, the brain computer user interface may include multiple elements that each elicits a unique sensory evoked response to guide and navigate the device. In some implementations, the first element can be selected if the indication of the attention of the subject to first sensory stimuli is greater than the indication of the attention of the subject to the second sensory stimuli and the second element can be selected if the indication of the attention of the subject to second sensory stimuli is greater than the indication of the attention of the subject to the first sensory stimuli. In some implementations, the selection of the first or second element can initiate the execution of a software application, software command or an electronic communication (or portion thereof). In some implementations, the user interface can include more than two elements, and an element that elicits the highest indication of the attention of the subject is selected. For example, the user interface can include multiple executable applications that may be launched, or multiple words or symbols that may be selected to construct a communication. Systems and methods relating to a brain computer user interface are discussed further below.

In some implementations, a time-locked sensory stream may be presented to respondents. The sensory evoked attention response of the respondents to specific attributes in the sensory stream is computed. The values of the individual signal features of the sensory evoked attention response, such as the amplitude of the peaks, classify the attended attribute of the sensory stimuli in real time. In some implementations, the sensory evoked response signal features of the attended attributes in the sensory stimuli are compared to the sensory evoked response of the unattended attributes of the sensory stimuli.

In some implementations, a machine learning interface can predict an attentional response of a subject to a new segment of speech. In one example subjects are first presented with naturalistic speech streams and instructed to either attend or ignore those naturalistic speech streams. The cross-correlation function may be computed between the naturalistic speech envelope and the EEG response across multiple time segments and averaged corresponding to the attended to and to the ignored conditions. The values derived from the envelope response are stored, including the latencies, the amplitudes, and the polarities of the cross-correlation peaks. Then, the data may be split into a training set and a test set. The features for the EEG channel that have the greatest difference between neural responses to the attended to and ignored conditions are used as the primary features. In addition, the features from the best channel, a selection of channels in a defined region, or all the channels may be input as features into the classifier. In some implementations, either a grid search or a random search with cross validation is utilized to search through the parameter space defined by the machine learning classifier. After training, the classifier may be used to classify the attentional response of a subject to a new segment of speech based on the sensory evoked response of the subject to the stimuli. The performance of the classifier may be evaluated by comparing the classifier's predictions on data in the test set against the true test data classifications. In some implementations, the data to train the machine learning classifier may be derived from an individual. In some implementations, the data to train the machine learning classifier may be derived from a population.

Figure 4:
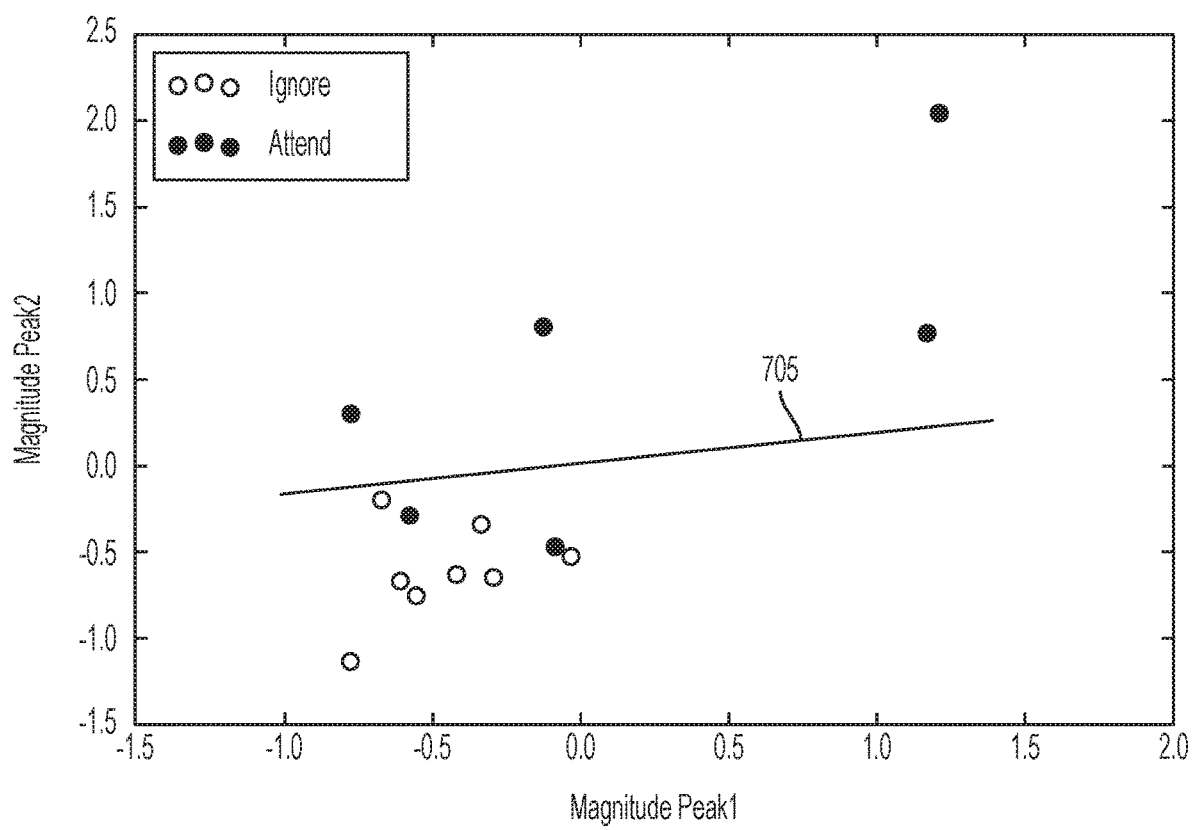
FIG. 4 shows an example of a machine learning model classification (support vector machine) of attention to speech in a subject.

FIG. 4 shows an example of a machine learning classification model, using a support vector machine classifier, to classify the subject's attention to speech. The classification of attention shown in FIG. 4 is based on the magnitude of two different peaks, Peak 1 and Peak 2, of the subject's sensory evoked response. The peaks located above the line 705 are indicative of the subject paying attention to the speech stimuli, while peaks located below the line 705 are indicative of the subject ignoring the speech stimuli.

FIGS. 5-8 show various examples of a sensory evoked natural speech envelope response to attended and ignored speech stimuli. As mentioned above, attention of a subject to a sensory stream may enhance the magnitude of the sensory evoked response signal of the subject, suppress the neural response of the ignored sensory stream, modulate the spatial distribution of the sensory evoked response, or shift the latency of the sensory evoked response. Accordingly, different sensory evoked responses can be compared by comparing the magnitudes of the peak values in the corresponding sensory evoked response signals.

Figure 5A:
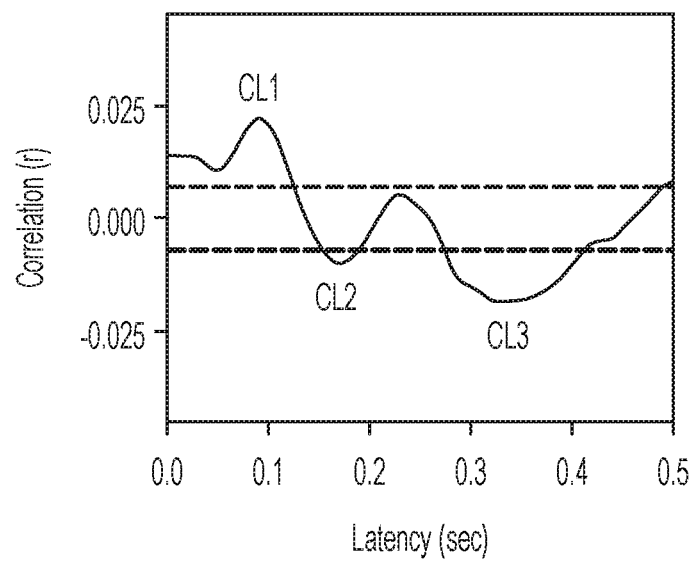
FIG. 5A and FIG. 5B illustrates an example plot of a representative individual natural speech envelope response in an attention task for a healthy control.
Figure 5B:
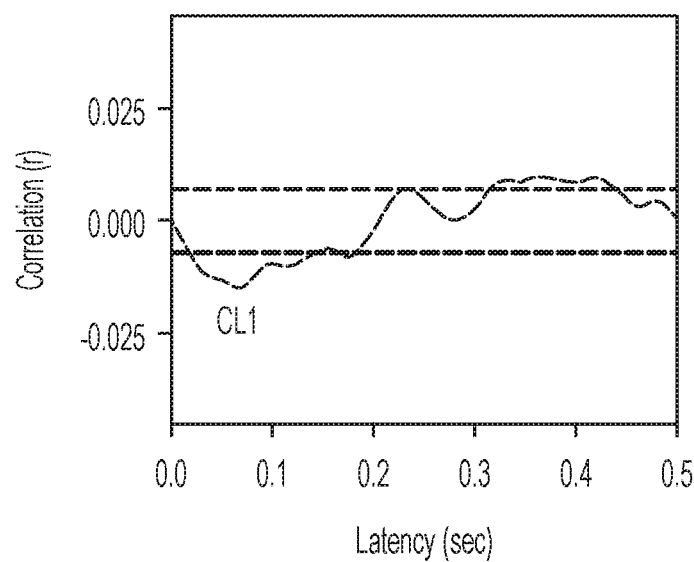

FIG. 5A and FIG. 5B illustrates a plot of representative sensory evoked responses of individuals to natural speech (calculated based on the natural speech envelope) in an attention task for a healthy control subject. In the task, the subject was asked to either attend or ignore the stimulus. FIG. 5A illustrates the subject's sensory evoked response during the attention condition, and FIG. 5B illustrates the subject's sensory evoked response during the ignore condition. In the attend condition the natural speech envelope shows three prominent peaks at CL1, CL2, and CL3, but the ignore condition only shows one peak at CL1. FIG. 5A illustrates that the attending can be distinguished from ignoring based on the magnitudes of the CL1, CL2, and CL3 peaks of a subjects sensory evoked response signal.

Figure 6B:
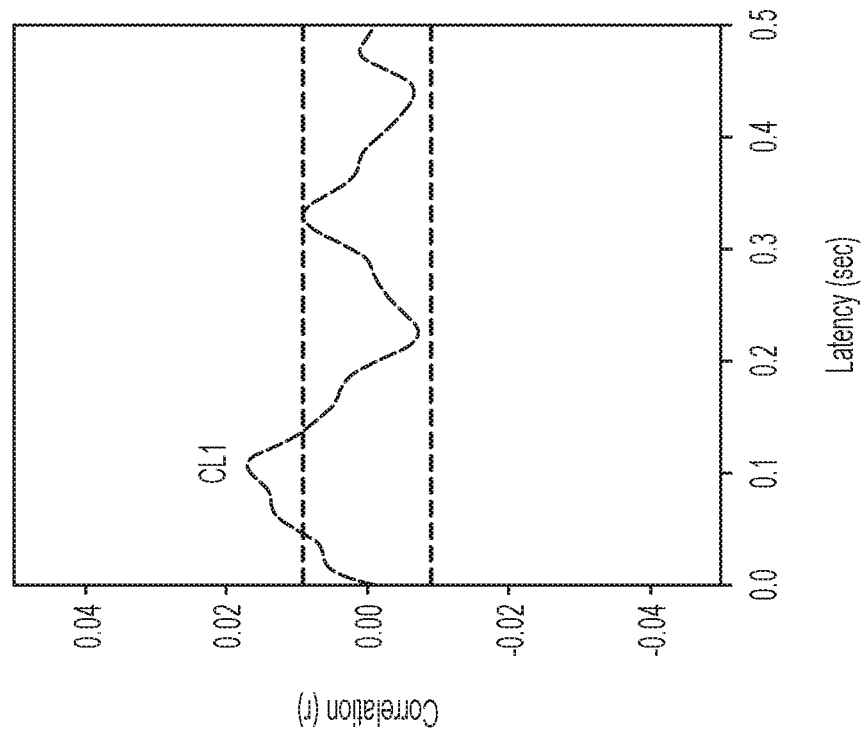
FIG. 6A and FIG. 6B illustrate a plot of representative sensory evoked responses of individuals to natural speech (calculated based on the natural speech envelope) in a dichotic listening trial for a minimally conscious patient with evidence of fMRI command following.
Figure 6A:
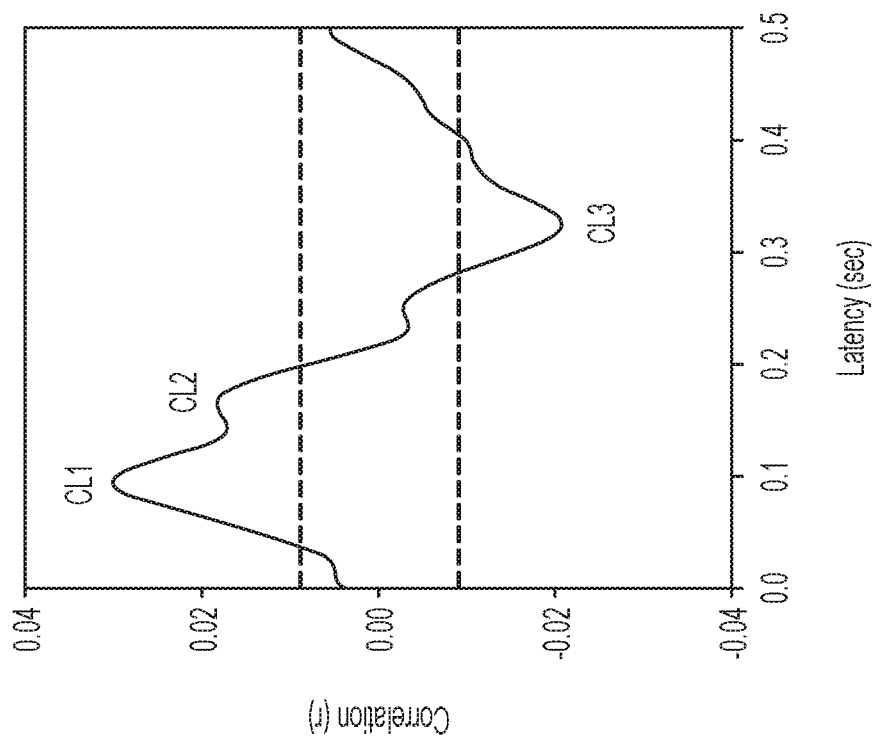

FIG. 6A and FIG. 6B illustrate a plot of representative sensory evoked responses of individuals to natural speech (calculated based on the natural speech envelope) in a dichotic listening trial for a minimally conscious patient with evidence of fMRI command following. FIG. 6A shows the patient's sensory evoked response during the attention condition. FIG. 6B shows the patient's sensory evoked response during the ignored condition. Similar to FIGS. 5A and 5B, the attended to condition in FIG. 6A shows three prominent peaks at CL1, CL2, and CL3, whereas, the ignored condition in FIG. 6B only shows one peak at CL1. The differences between the attended-to and ignored conditions in sensory evoked natural speech envelope are illustrated in the magnitudes of the CL1, CL2, and CL3 peaks, where the larger magnitudes show a larger sensory evoked response to the stimuli based on the subject's attended-to condition.

Figure 7:
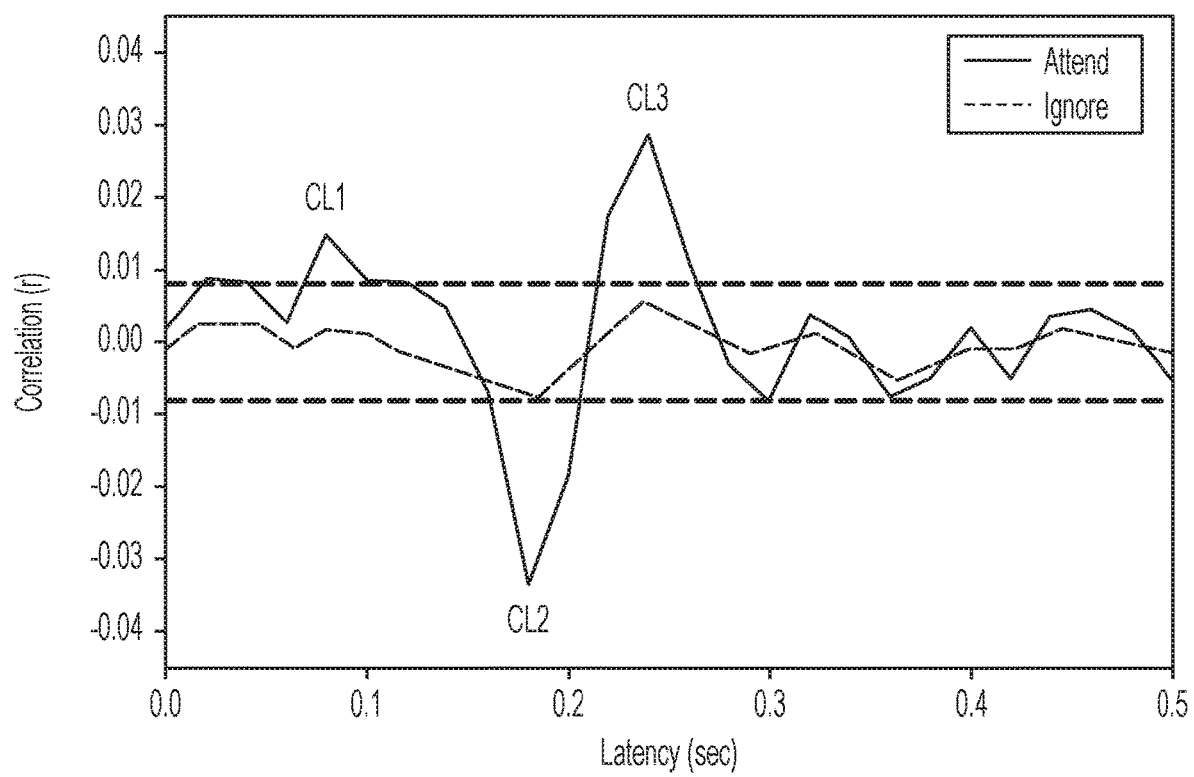
FIG. 7 illustrates an example plot of a representative sensory evoked response of an individual to an attended-to aperiodic visual stimulus.

FIG. 7 illustrates an example plot of a representative sensory evoked response of an individual to an attended to aperiodic visual stimulus. The aperiodic visual stimuli were aperiodic modulations of the luminosity of an image. The subject's attended-to sensory evoked response to the visual stimuli (solid line) shows the magnitude values as the first peak (CL1), the second peak (CL2), and the third peak (CL3). The ignored response (dashed line) shows how the sensory evoked response would look if the subject was asked to ignore the visual stimuli. In the ignore condition the sensory evoked response would remain around a correlation value of about 0.0, whereas the magnitude values of CL1, CL2, and CL3 all reach significant correlation values (as shown by the dotted horizontal lines). Similar to FIGS. 6A and 6B, the larger magnitude values show a larger sensory evoked response to the aperiodic visual stimuli based on the subject's attended-to condition.

Figure 8:
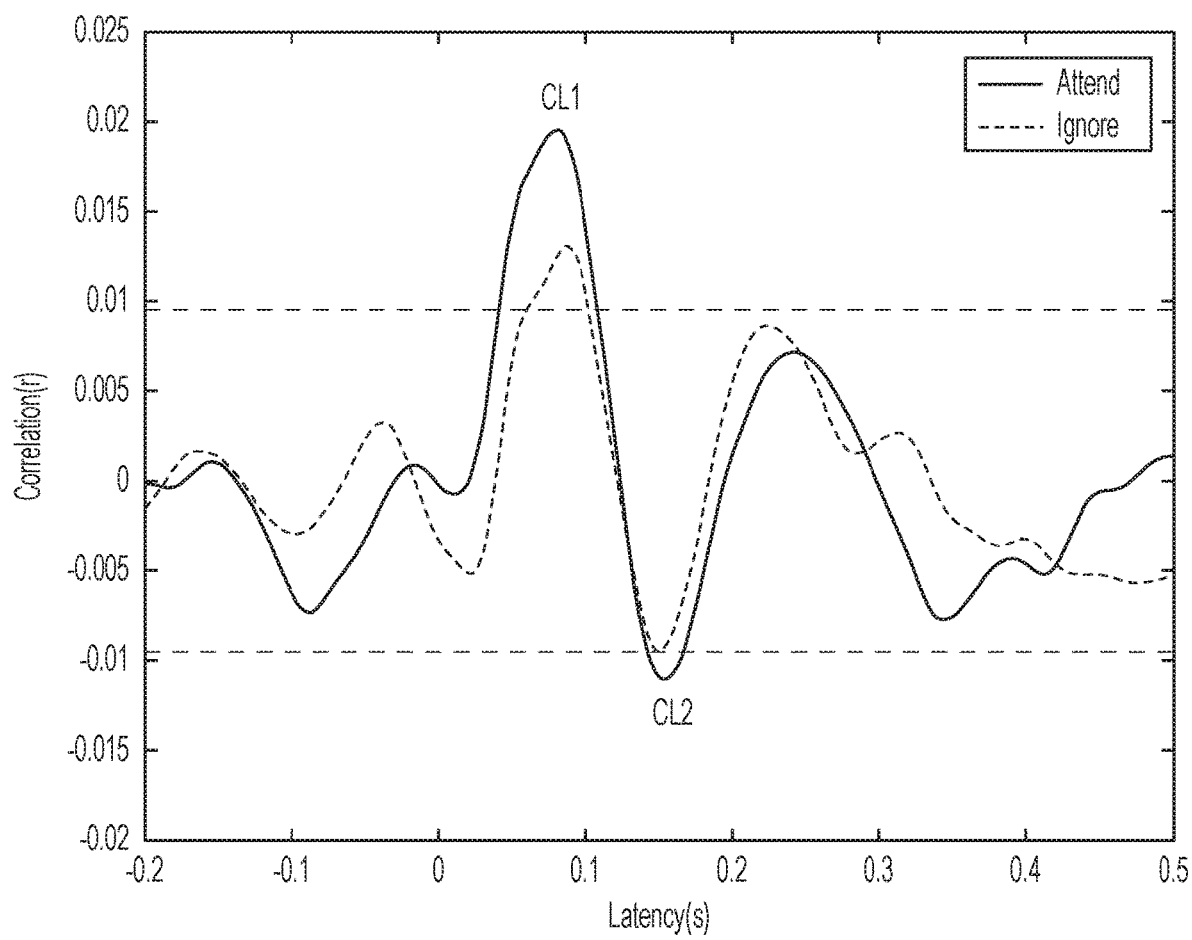
FIG. 8 shows a grand average natural speech envelope response across a group of subjects to attended and ignored speech stimuli.

FIG. 8 shows a grand average natural speech envelope response across a group of eight subjects to attended speech stimuli and ignored speech stimuli. The subjects were asked to first listen to and pay attention to a naturalistic speech stimulus. The Figure demonstrates that the phenomena of increased magnitude peaks in the attended to condition is robust across multiple subjects. In FIG. 8, the attended stimuli (solid line) shows a larger magnitude value than the ignored stimuli (dashed line) for both the CL1 and CL2 peaks. Accordingly, the systems and methods disclosed herein can be used to determine which stimuli a subject pays greater attention to by evaluating the magnitude of the peaks of the subjects sensory evoked response signal resulting from the subject being exposed to the stimuli. A subject's indication of attention can be used to select future content for communication, as described in FIG. 10, or for triggering further computer processing, such as a computer brain user interface, described further below.

In some implementations, systems and methods according to the present disclosure provide an EEG or ECoG based augmentation tool for neuroprosthetics such as EEG enhanced hearing aids, EEG enhanced headphones/earphones or neuroprosthetic development. Hearing loss due to injuries or aging may require hearing aids or cochlear implants. However, the current hearing aids may be unable to suppress distracting noise or enhance relevant auditory signals. Furthermore, cochlear implants rely on frequency domain analysis of auditory signals rather than the speech envelope. By identifying audio signals the subject is attending based on their corresponding sensory evoked response signals, EEG or ECoG enhanced hearing aids may use the sensory evoked response signal to enhance relevant and attended signals, suppress noise and ignored input, and enhance the signal fidelity. This approach may more effectively treat the higher level perceptual aspect of hearing loss allowing for a measure of processing of naturalistic stimuli to aid, for example, in the adjustment of an early stage neuronal input.

Prosthetic development and use may be improved with a continuous measure of neural-prosthetic coupling in the auditory, visual, and somatosensory modalities. For example, a neural measure of an auditory prosthetic through the envelope response may determine attention and other neural signals that may guide the prosthetic use. Because the auditory envelope is robust and long-lasting and linked to the multi-second auditory working memory buffer this approach may allow for broad and sustained, over time, integration of multi-sensory signals to aid acquisition of use of different neuroprosthetics. In some implementations, EEG enhanced headphones may consist of a sensor placed over temporal channels connected wirelessly to a set of headphones. The sensor may utilize the neural information to modulate the auditory signal to enhance or suppress attended or ignored signals using the methodology described above.

Figure 9:
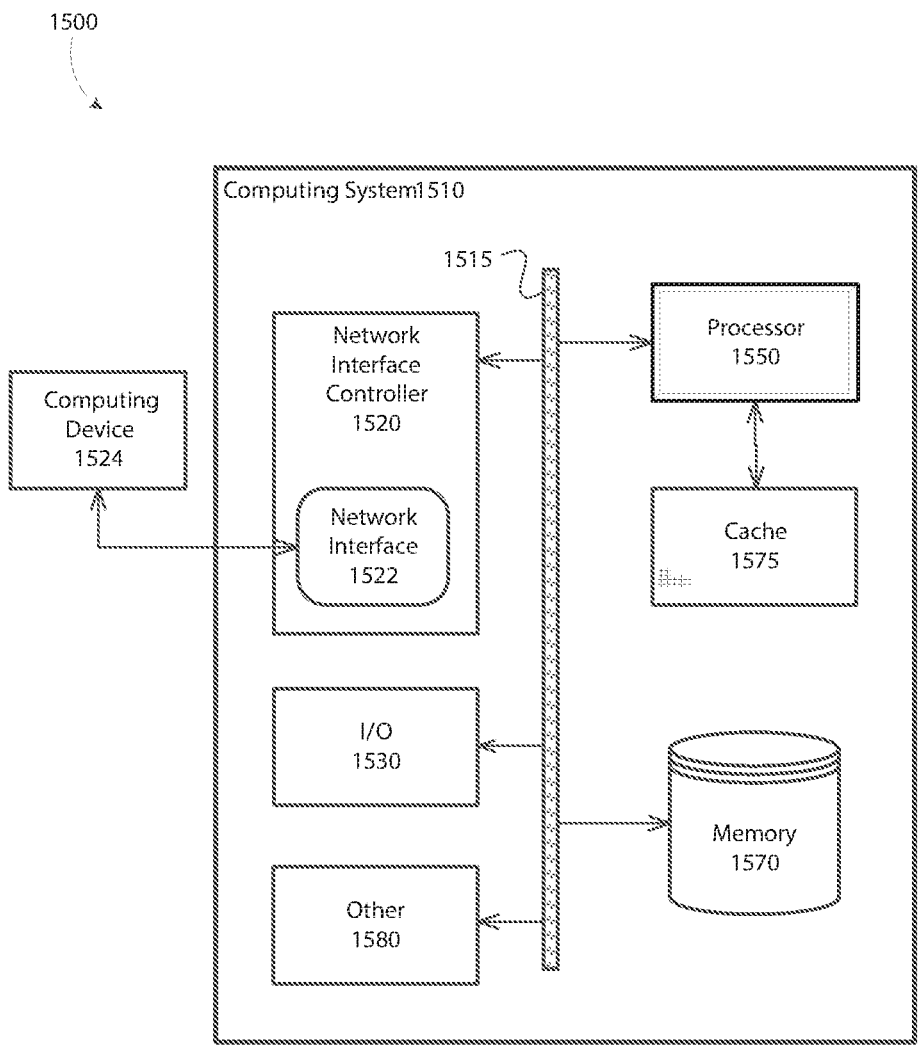
FIG. 9 illustrates a block diagram of an example computing system.

FIG. 9 illustrates a block diagram of an example computing system 1500. In some implementations, the computing system 1500 may be utilized in implementing the systems and methods in FIGS. 1-3 above.

In broad overview, the computing system 1510 includes at least one processor 1550 for performing actions in accordance with instructions and one or more memory devices 1570 or 1575 for storing instructions and data. The illustrated example computing system 1510 includes one or more processors 1550 in communication, via a bus 1515, with at least one network interface controller 1520 with network interface ports 1522($a$-$n$) connecting to other computing devices 1524($a$-$n$), memory 1570, and any other devices 1580, e.g., an I/O interface. Generally, a processor 1550 will execute instructions received from memory. The processor 1550 illustrated incorporates, or is directly connected to, cache memory 1575.

In more detail, the processor 1550 may be any logic circuitry that processes instructions, e.g., instructions fetched from the memory 1570 or cache 1575. In many embodiments, the processor 1550 is a microprocessor unit or special purpose processor. The computing device 1500 may be based on any processor, or set of processors, capable of operating as described herein. In some implementations, the processor 1550 can be capable of executing the diagnostic system methods shown in FIGS. 1-3. The processor 1550 may be a single core or multi-core processor. The processor 1550 may be multiple processors. In some implementations, the processor 1550 can be configured to run multi-threaded operations. In some implementations, the processor 1550 may host one or more virtual machines or containers, along with a hypervisor or container manager for managing the operation of the virtual machines or containers. In such implementations, one or more of the methods 1300 and 1400 shown in FIGS. 1-3 can be implemented within the virtualized or containerized environments provided on the processor 1550.

The memory 1570 may be any device suitable for storing computer readable data. The memory 1570 may be a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, and BluRay® discs). A computing system 1500 may have any number of memory devices 1570. In some implementations, the memory 1570 supports virtualized or containerized memory accessible by virtual machine or container execution environments provided by the computing system 1510.

The cache memory 1575 is generally a form of computer memory placed in close proximity to the processor 1550 for fast read times. In some implementations, the cache memory 1575 is part of, or on the same chip as, the processor 1550. In some implementations, there are multiple levels of cache 1575, e.g., L2 and L3 cache layers.

The network interface controller 1520 manages data exchanges via the network interfaces 1522($a$-$n$) (also referred to as network interface ports). The network interface controller 1520 handles the physical and data link layers of the OSI model for network communication. In some implementations, some of the network interface controller's tasks are handled by the processor 1550. In some implementations, the network interface controller 1520 is part of the processor 1550. In some implementations, a computing system 1510 has multiple network interface controllers 1520. The network interfaces 1522($a$-$n$) are connection points for physical network links. In some implementations, the network interface controller 1520 supports wireless network connections and an interface port 1522 is a wireless receiver/transmitter. Generally, a computing device 1510 exchanges data with other computing devices 1512($a$-$n$) via physical or wireless links to a network interfaces 1522(a-n). In some implementations, the network interface controller 1520 implements a network protocol such as Ethernet.

The other computing devices 1524(a-n) are connected to the computing device 1510 via a network interface port 1522. The other computing devices 1524(a-n) may be peer computing devices, network devices, or any other computing device with network functionality. For example, a first computing device 1524(a) may be a network device such as a hub, a bridge, a switch, or a router, connecting the computing device 1510 to a data network such as the Internet.

The other devices 1580 may include an I/O interface, external serial device ports, and any additional co-processors. For example, a computing system 1510 may include an interface (e.g., a universal serial bus (USB) interface) for connecting input devices (e.g., a keyboard, microphone, mouse, or other pointing device), output devices (e.g., video display, speaker, or printer), or additional memory devices (e.g., portable flash drive or external media drive). In some implementations, a computing device 1500 includes an additional device 1580 such as a coprocessor, e.g., a math co-processor can assist the processor 1550 with high precision or complex calculations.

Example Content Selection Applications

Referring to FIGS. 1 through 3, FIG. 10 illustrates a flow diagram of an example method 1300 for selecting content for future communication based on a subject's indication of attention. Method 1300 includes receiving a measurement of a neural response of a subject to one or more first sensory stimuli (step 1305A) and receiving information related to the one or more first sensory stimuli (step 1310A). Method 1300 also includes receiving a measurement of a neural response of the subject to one or more second sensory stimuli (step 1305B) and receiving information related to the one or more second sensory stimuli (step 1310B). Method 1300 further includes determining a first indication of the attention of the subject to the first sensory stimuli (step 1315A) and determining a second indication of the attention of the subject to the second sensory stimuli (step 1315B). Next, method 1300 includes comparing the first indication of attention of the subject to the second indication of the attention of the subject to determine which stimuli resulted in the greater level of attention (step 1320). Finally, the method 1300 includes selecting content for a future communication based on the stimulus that elicited the greater level of attention (step 1330).

Similar to method 300 shown in FIG. 3, method 1300 includes receiving a measurement of the neural response of the subject to one or more first sensory stimuli (step 1305A) and receiving information related to the one or more first sensory stimuli (step 1310A). Method 1300 also includes receiving a measurement of the neural response of the subject to one or more second sensory stimuli (step 1305B) and receiving information related to the one or more second sensory stimuli (step 1310B).

As mentioned above in FIG. 3, determining a first indication of the attention of the subject to the first sensory stimuli (step 1315A) includes determining a statistical relationship between a characteristic of the one or more sensory stimuli from step 1310A and the received measurement of the neural response from step 1305A. Similarly, determining a second indication of the attention of the subject to the second sensory stimuli (step 1315B) includes determining a second statistical relationship between a characteristic of the one or more sensory stimuli from step 1310B and the received measurement of the neural response from step 1305B. The sensory evoked response represents the statistical comparison between the EEG signal and either the raw stimulus signal or the stimulus signal envelope.

Next, method 1300 includes comparing the determined first indication of the attention of the subject from step 1315A to the second indication of the attention of the subject from step 1315B in order to determine which stimulus resulted in the greater level of attention (step 1320). The result of the comparison can be based on the signal features of the corresponding sensory evoked response signals. Similar to FIG. 3, a magnitude value corresponding to a peak value of the statistical relationship between the sensory stimuli and the neural responses may indicate the level of attention of the subject. In some implementations, other signal features, including latency, may indicate the level of attention of the subject.

Next, method 1300 includes selecting content for a future communication based on the content that elicited the greater level of attention from step 1320 (step 1330). In some implementations, the content selection may be a voice, alarm sound, or word choice that can be included in a safety alert or warning sign. Such a method can be used, e.g., to improve industrial safety or safety warnings in other potentially dangerous environments. In some implementations, the content may include content to include in education materials, so that the systems and methods can be used to help improve education materials for students by identifying content that elicits the greater level of attention in the academic setting. Such selection can be between different word choices, different phrasing, or for audio or visual content, between different audio or visual sequences that convey academic material. In some implementations, the content may be selected for use in generating more attended to marketing materials. Additional examples of content selection for future communications are discussed further below.

In some implementations, the present method 1300 for selecting content or future communication may be modified based on the results in step 1330. For example, the method 1300 may be modified based on the evaluation of the sensory evoked responses derived from the presentation of the same stimuli to multiple subjects. In some implementations, the method 1300 may be repeated for subjects from different demographics, thereby identifying content that may be more useful in communications to each respective demographic group tested, or for content which would be the most advantageous for use across multiple demographics, for example based on a mean or median attention level determined based on each subjects sensory evoked response to the content. In some implementations, the method 1300 may be repeated for subjects using auditory stimuli in different voice tones or using different languages or pitches. In some implementations, the method according to FIG. 10 may use naturalistic audio-video stimuli with different colors, sounds, lengths and volumes to elicit the greater indication of attention.

Education providers may use EEG or ECoG based sensory evoked responses to a single or multi-modal naturalistic auditory, visual, and somatosensory sensory streams as a measure of attention, familiarity, and emotional response to education-based learning materials to help students learn material in the classroom. In some implementations, computerized educational software tests a student's familiarity of a topic and a student's ability to attend to relevant information and ignore distractions. In an example implementation, an EEG-based system that incorporates neural measures of the auditory envelope to a learned auditory stream may monitor a student's progress by indexing attention and familiarity and selecting attended to stimuli for future communication. In addition, the auditory envelope response may be utilized in conjunction with visual evoked response to natural fluctuations in the luminosity amplitude or steady state fluctuations on a display screen to attended items and to subtle naturalistic or aperiodic somatosensory vibrations on the mouse or pencil and pen to measure the coupling between a student's motor movements to the educational material.

In an example implementation, a teacher may want to determine how individuals are responding to the latest education materials or the latest lesson plan. The education materials may be an audio stimulus, a visual stimulus, or an audio-video stimulus. In some implementations, the student may wear headphones to listen to the audio educational materials. In some implementations, the educational materials may be playing on as a video stream, and in some implementations, the student may be listening to and viewing the educational materials. Referring to FIG. 10, the current systems and methods can compare the student's response to different forms of educational materials, and select the materials that elicited the greater level of attention, allowing for more personalized education.

In another implementation, the student may be presented with the educational materials as well as a distracting stimulus or noise. The sensory evoked response can be indicative of whether the materials successfully captured the student's attention based on comparing the attention of the subject to the education materials versus the distracting stimulus. Referring to FIG. 10, the sensory evoked response of the attended materials may be selected and incorporated into future educational communications.

Through advanced machine learning approaches, attention to individual words in a lesson plan may be evaluated and selected for future communications. Furthermore, with ECoG, an instantaneous and highly accurate attention and familiarity-based response may be determined that can select future educations materials in real time, thereby improving the student's on-going lesson. In some implementations, the naturalistic auditory streams may be coupled to flickering or naturalistic visual streams in the classroom. In some implementations, systems and methods according to the present disclosure provide EEG enhanced education software for testing or language learning/dyslexia.

As suggested above, industrial companies may use EEG or ECoG based sensory evoked responses to a single or multi-modal auditory, visual, and somatosensory sensory streams as a measure of attention, familiarity, and emotional response to industrial-based safety warnings to prevent accidents in the workplace.

In an example implementation, an industrial company may want to determine how individuals are responding to the company's latest safety warning. A group of subjects may be presented with the safety warning. In some implementations, the safety warning may be audio warning, such as an intercom announcement. In some implementations, the safety warning may be a visual warning, such as a sign. And in some implementations, the safety warning may be a combination of audio-visual stimuli. The sensory evoked response of the subject in response to the presented safety warning is measured, and a statistical relationship computed between the safety warning stimuli and the neural response thereto. Then, the magnitude of the peaks of the computed sensory evoked response can indicate the attention of the subject while exposed to the safety warning. In some implementations, a subject may be presented with two safety warnings in sequential order, where the safety warnings can be for products or dangerous situations that require a person's attention and the current methods can determine which warning generated the greater attended-to response in the subject.

In some implementation, the safety warnings may be playing simultaneously in separate ears, and the systems and methods of the current disclosure can select which safety warning the subject pays more attention to. In another implementation, the subject may be presented with the safety warning as well as a distracting stimulus or noise. The sensory evoked response can be indicative of whether the warning successfully captured the subject's attention based on comparing the attention of the subject to the warning versus the distracting stimulus. Using the current systems and methods disclosed herein, the sensory evoked response of the attended audio warning may be selected and incorporated into future communications.

In some implementations, the safety warning may be a visual warning, such a sign. The neural response of a subject to the visual warning can be measured and cross-correlated with the modulation patterns. In some implementations, the cross-correlation signal associated with each feature and corresponding modulation pattern can be used as a sensory evoked response signal for evaluating the subject's attention to the safety warning. Various features of the sensory evoked response signals for the warning can be evaluated and compared in order to identify the location and the strength of the attention response to the various features in the visual stimulus. Such signal features include, for example, latencies of peaks, peak amplitudes, polarities, and spatial distribution (i.e., distribution across multiple EEG electrodes) of the signal. A group of subjects can be presented with a first and second version of a visual warning. The different versions may employ different imagery, different speech content, different voices, or other modifications to the sensory content of the warning. The sensory evoked response of the subject in response to the first and second version of the warning is computed. The magnitude of the peaks of the computed sensory evoked response for each version can indicate the attention of the subject while viewing that version of the warning. In some implementations, a manufacture can measure the attention of the subject to sensory stimuli in order to tailor its warning signs across various demographic segments. For example, based on the aforementioned testing, it may be determined that a first demographic may pay greater attention to a first voice profile while a different demographic may pay greater attention to a different voice profile. Accordingly, appropriate voiceovers may be applied to advertisements intended for viewing by the different demographics or a voiceover can be selected that will have be paid attention to by the broadest audience.

As suggested above, In some implementations, neuromarketing companies may use an EEG or ECoG based sensory evoked responses to a single or multi-modal naturalistic auditory, visual, and somatosensory sensory streams as a measure of attention, familiarity, and emotional response to radio, television, mobile-based, and web-based commercials. In some implementations, competing auditory speech streams or voices may be presented to determine a subject's attention and preference to an item, person of interest, voice, model, or commercial. In an example implementation, in a television commercial, a subject's voice may be coupled with a naturalistic visual stream or frequency-tagged flickering item or object on the screen such that a multi-modal attention based response to an object or individual in a commercial may be assessed in multiple modalities.

Figure 11:
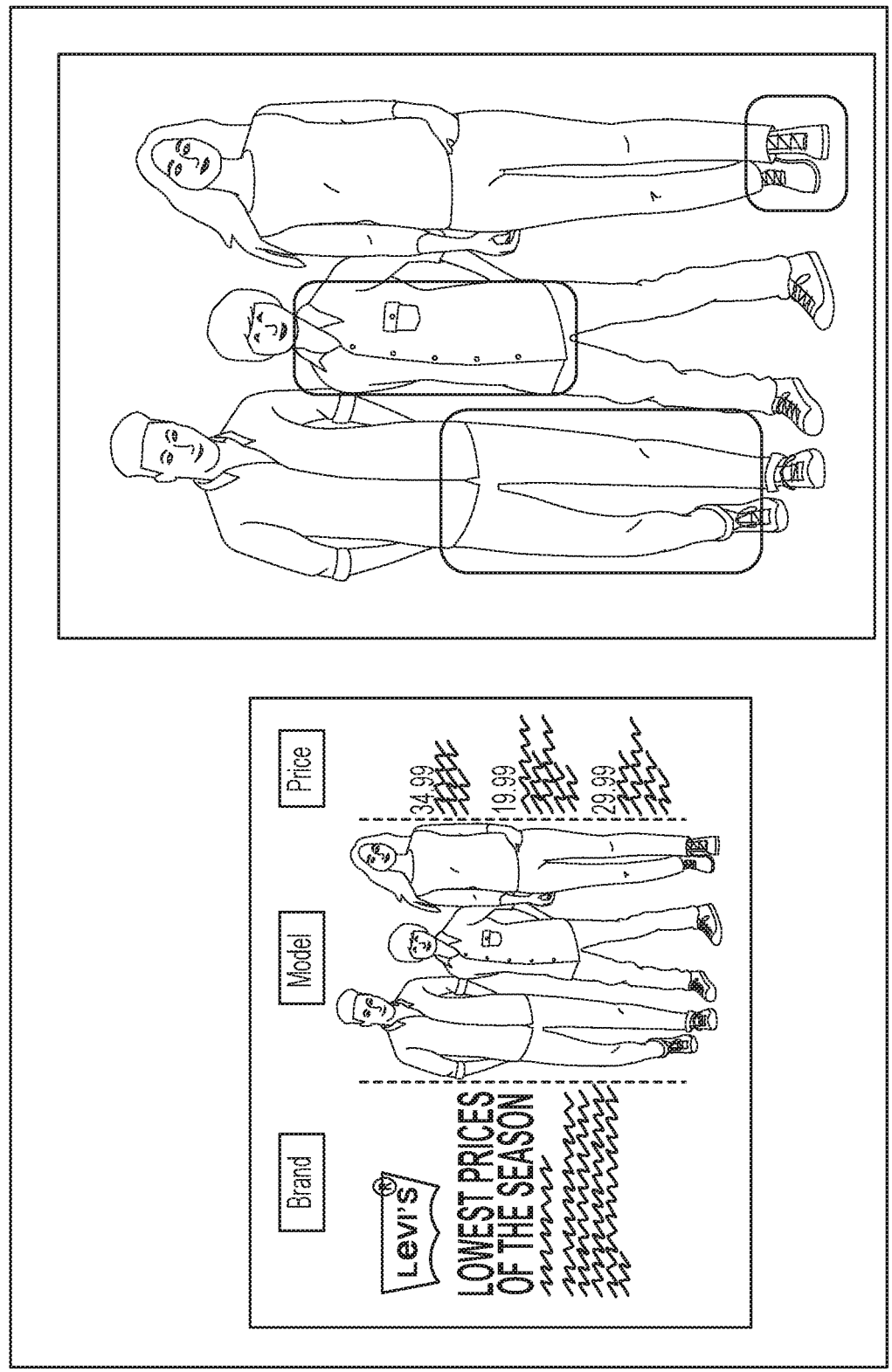
FIG. 11 shows an example of a visual market research stimulus with the features such as price, brand, and model labeled accordingly.
Figure 12:
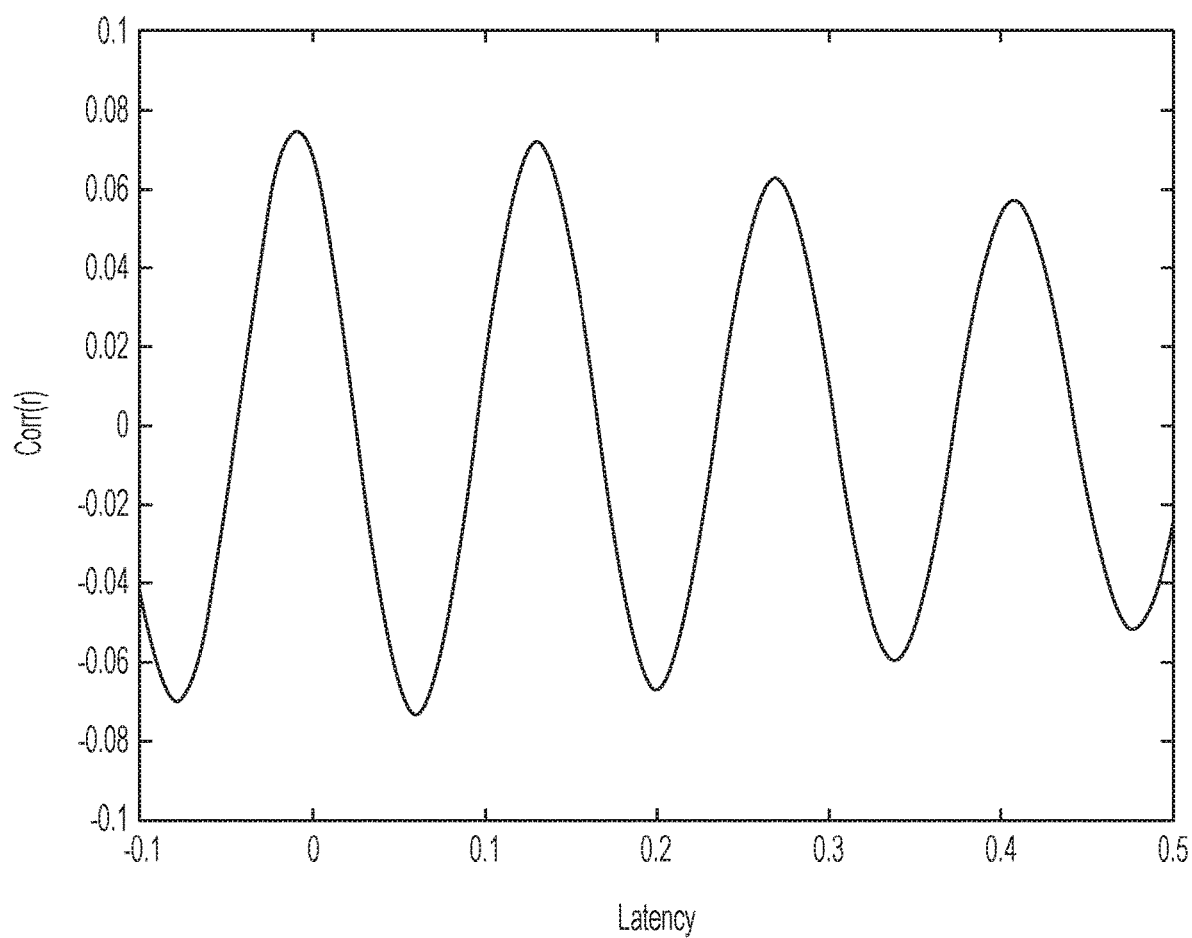
FIG. 12 shows a visual sensory evoked response to an attribute of a visual advertisement.

In some implementations, a market research company may want to determine consumer response to visual advertisements. FIG. 11 shows an example of a visual market research stimulus or advertisement with the features such as price, brand, and model labeled accordingly. In some implementations, the features may be assigned with visual modulation patterns. Visual modulation patterns may include modulation of the contrast, brightness, or color of the regions of the visual stimulus in which the features are located. In some implementations, a subject or viewer may be shown the visual market research stimulus while specific features are modulated based on their respective assigned modulation patterns. In some implementations, attributes of visual stimuli may be modulated with a unique superimposed time series. In various implementations, the modulated pattern may be periodic, quasi-periodic or aperiodic. Wherein the aperiodic sensory stimuli refers to a naturalistic sensory signal. Each feature can elicit a unique sensory evoked response in the viewer. FIG. 12 shows a visual sensory evoked response to an attribute or feature of a visual advertisement, such as the visual stimulus shown in FIG. 11. In some implementations, a market research company may want to determine how consumers are responding to different versions of an advertisement and tailor their marketing based on the results.

In some implementations, in the context of market research, the EEG neural response and behavioral responses may be input as features into a regression or classification model to predict the consumer decisions, the purchasing behavior, and to identify the words or features that resonate with consumers. In some Implementations, the attention response may be measured between two or more sensory stimuli of the same or different modalities. In addition, the neural response of only one stimulus may be compared between attend and ignore conditions.

In some implementations, systems and methods according to the present disclosure provide an indication of the intention of the subject.

For selecting content in any form of future communication, the sensory evoked response or sensory evoked attention response may reveal the order, duration, and strength of attention to the attributes of the stimuli, including words and images. For visual stimuli, the sensory evoked attention response may be referenced to the location and duration of the subject's eye tracking. In some implementations, the sensory evoked attention response may also be referenced to the results of the recall, recognition, and persuasion tests utilized to assess stimulus effectiveness. The sensory evoked attention response may correlate with the recall of a subject to previously presented stimuli. In some implementations, a machine-learning regression or classification model that utilizes the features of the sensory evoked attention response may predict or identify the most effective attributes of sensory stimuli.

Applications for a Brain Computer Interface

In some implementations, systems and methods according to the present disclosure provide an EEG or ECoG and auditory based Brain Computer Interfaces (BCIs) such as touch-free mind-controlled devices. Touch-free mind-controlled devices may be navigated or controlled through a user intentionally attending to various streams of sensory information output via a user interface. The sensory streams may include naturalistic or periodic speech, flickering or naturalistic visual input, and/or vibrating naturalistic or periodic somatosensory input. The attention of the user to the single or multi-modal input streams and its resulting modulation of the envelope and steady state response of the sensory evoked response may be employed to guide and navigate the touch-free devices such as laptops, computers, tablets, e-books, smartphones, televisions, gaming consoles, virtual reality devices, web navigation, and other technological devices. For example, a tablet with a set of applications may contain icons for applications that flicker at a unique frequency or otherwise have their graphic appearance modulated over time, either with unique graphical modulation patterns, or by emitting a unique naturalistic visual stream, a corresponding unique auditory envelope, and/or unique somatosensory vibrating periodic or naturalistic pattern. The attention of the user to a particular application icon in the auditory, visual, or somatosensory domains may be detected and used to launch and then navigate the user through the application. In some implementations, each user interface element (e.g., icon or button) within the application may further emit unique sensory stimuli to guide the user's next action. Touch-free mind-controlled devices according to some implementations may be provided for motor-impaired users as well as non-motor-impaired users.

Typical BCIs rely on visual steady state response, imagined motor movements, and event-related responses. However, in severe brain-injured patients, the visual system may be impaired and motor planning and movement may be challenging. Current auditory brain-computer interfaces are guided by the neural response to unnatural transient and repetitive event-related potential paradigms. In the auditory oddball paradigm, streams of deviant and standard stimuli are presented in the right and left ears. An enhanced event-related response is elicited with an attentional response to the deviant target stimulus. However, as compared to a visual stimuli, the auditory stimuli may have a reduced user performance and a diminished information transfer rate. In some implementations, an envelope-based approach may provide a continuous and naturalistic high information input for an improved auditory brain computer interface. The envelope-based auditory brain computer interface may significantly improve communication in motor-impaired patients with severe brain injury, ALS, and immobile aging patients. In some implementations, the envelope response may determine an attention-mediated response in single trials. In some implementations, the envelope response may be determined by a cross-correlation coupled with machine learning algorithms, such as linear discriminant analysis and may accurately determine the direction of attention at an accuracy rate.

In some implementations, the use of ECoG may significantly enhance the quality of the measured neural signal, reduce artifacts, and enhance spatial resolution. In some implementations, the use of ECoG may significantly improve the accuracy and speed of single-trial EEG-based brain computer interfaces. In some implementations, the ECoG signal may determine an instantaneous real time index of the envelope response to guide a more effective, sensitive, and precise next generation auditory brain computer interface. In some implementations, systems and methods according to the present disclosure provide EEG or ECoG based military applications for telemetry and covert communication. Motor-independent brain computer interfaces that read a subject's intentions may also be used for communication purposes. In some implementations, a first subject's attentional selection of an auditory input stream may be transferred to a second subject. In some implementations, the motor-independent communication interface may utilize a single or multiple electrodes and a set of headphones.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted that the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A method comprising:
receiving, by a processor, a measurement of a neural response of a subject to a first sensory stimuli and a second sensory stimuli, wherein the first sensory stimuli corresponds to a first user-actuatable element of a user interface and the second sensory stimuli corresponds to a second user-actuatable element of the user interface;
receiving, by the processor, information related to the first sensory stimuli and the second sensory stimuli, wherein the information includes at least one signal feature of the first sensory stimuli and the second sensory stimuli;
determining, by the processor, a statistical relationship between the at least one signal feature of the first sensory stimuli and the second sensory stimuli and the measurement of the neural response of the subject;
identifying, by the processor, a first magnitude value comprised of a peak value of the determined statistical relationship between the at least one signal feature of the first sensory stimuli and the measurement of the neural response of the subject, and a second magnitude value comprised of a peak value of the determined statistical relationship between the at least one signal feature of the second sensory stimuli and the measurement of the neural response of the subject;
determining, by the processor, a first indication of the attention of the subject to the first sensory stimuli based on the identified first magnitude value, and a second indication of the attention of the subject to the second sensory stimuli based on the identified second magnitude;
comparing, by the processor, the determined first indication of attention of the subject to the determined second indication of the attention of the subject; and
selecting, by the processor, between the first user-actuatable element of the user interface and the second user-actuatable element of the user interface based on which user-actuatable element elicited the greater indication of the attention of the subject; and,
triggering, by a computer, further computer processing based on the selection of the user-actuatable element, wherein triggering further computer processing comprises actuating the selected element of the user interface.

2. The method of claim 1, wherein the sensory stimuli includes at least one of an auditory, visual, or somatosensory stimuli.

3. The method of claim 1, wherein the statistical relationship is a cross-correlation analysis between at least one signal feature of the sensory stimuli with the received measurement of the neural response.

4. The method of claim 1, wherein the actuation of the first user-actuatable element causes the launch of a first software application or first software command and the actuation of the second user-actuatable element causes the launch of a second software application or second software command.

5. The method of claim 1, wherein the actuation of the first user-actuatable element causes the selection of a first word or first symbol for inclusion in a communication and the actuation of the second user-actuatable element causes the selection of a second word or second symbol for inclusion in a communication.

6. The method of claim 1, where the first and second user-actuatable elements comprise graphical icons on a device display.

7. A system comprising:

a plurality of stimuli devices configured to evoke a neural response of a subject;

one or more processors implementing a processing unit configured to determine an indication of the attention of the subject to a first sensory stimuli corresponding to a first user-actuatable element of a user interface and a second sensory stimuli corresponding to a second user-actuatable element of the user interface, by:

receiving a measurement of a neural response of a subject to the first sensory stimuli and the second sensory stimuli;

receiving information related to the first sensory stimuli and the second sensory stimuli wherein the information includes at least one signal feature of the first sensory stimuli and the second sensory stimuli;

determining a statistical relationship between the at least one signal feature of the first sensory stimuli and the second sensory stimuli and the measurements of the neural response of the subject;

identifying a first magnitude value comprised of a peak value of the determined statistical relationship between the at least one signal feature of the first sensory stimuli and the measurement of the neural response of the subject, and a second magnitude value comprised of a peak value of the determined statistical relationship between the at least one signal feature of the second sensory stimuli and the measurement of the neural response of the subject;

determining a first indication of the attention of the subject to the first sensory stimuli based on the identified first magnitude value, and a second indication of the attention of the subject to the second sensory stimuli based on the identified second magnitude;

comparing the determined first indication of attention of the subject to the determined second indication of the attention of the subject;

selecting between the first user-actuatable element of the user interface and the second user-actuatable element of the user interface based on which user-actuatable element elicited the greater indication of the attention of the subject; and, one or more computers configured to trigger further computer processing based on the selection of the user-actuatable element, wherein triggering further computer processing comprises actuating the selected element of the user interface.

8. The system of claim 7, wherein the sensory stimuli includes at least one of an auditory, visual, or somatosensory stimuli.

9. The system of claim 7, wherein the statistical relationship is a cross-correlation analysis between at least one signal feature of the sensory stimuli with the received measurement of the sensory evoked neural response.

10. The system of claim 7, wherein the actuation of the first user-actuatable element causes the launch of a first software application or first software command and the actuation of the second user-actuatable element causes the launch of a second software application or second software command.

11. The system of claim 7, wherein the actuation of the first user-actuatable element causes the selection of a first word or first symbol for inclusion in a communication and the actuation of the second user-actuatable element causes the selection of a second word or second symbol for inclusion in a communication.

12. The system of claim 7, where the first and second user-actuatable elements comprise graphical icons on a device display.

* * * * *